(12) United States Patent
Geddes

(10) Patent No.: US 9,719,923 B2
(45) Date of Patent: Aug. 1, 2017

(54) TUNING OF METAL ENHANCED EMISSIONS OF LONG-LIVED LUMINESCENT COMPOUNDS

(75) Inventor: Chris D. Geddes, Bel Air, MD (US)

(73) Assignee: UNIVERSITY OF MARYLAND, BALTIMORE COUNTY, Baltimore, MD (US)

(*) Notice: Subject to any disclaimer, the term of this patent is extended or adjusted under 35 U.S.C. 154(b) by 1133 days.

(21) Appl. No.: 13/697,042

(22) PCT Filed: May 11, 2011

(86) PCT No.: PCT/US2011/036025
§ 371 (c)(1),
(2), (4) Date: Jan. 15, 2013

(87) PCT Pub. No.: WO2011/143288
PCT Pub. Date: Nov. 17, 2011

(65) Prior Publication Data
US 2013/0115710 A1 May 9, 2013
US 2017/0067828 A9 Mar. 9, 2017

Related U.S. Application Data

(63) Continuation-in-part of application No. 12/016,247, filed on Jan. 18, 2008, now Pat. No. 9,023,372.
(Continued)

(51) Int. Cl.
*G01N 21/64* (2006.01)
*C09K 11/02* (2006.01)
(Continued)

(52) U.S. Cl.
CPC ........... *G01N 21/64* (2013.01); *C09K 11/025* (2013.01); *C09K 11/06* (2013.01);
(Continued)

(58) Field of Classification Search
CPC ........... C12Q 2563/155; C12Q 1/6834; C12Q 2525/161; C12Q 1/6816; C12Q 2525/197;
(Continued)

(56) References Cited

U.S. PATENT DOCUMENTS 4,576,912 A   3/1986  Yaverbaum et al.
7,095,502 B2  8/2006  Lakowicz et al.
(Continued)

FOREIGN PATENT DOCUMENTS

WO   WO2004024191   3/2004

OTHER PUBLICATIONS

Srivatsava and Faris. Covalent Attachment for Surface Enhancement of Lanthanide Emission, Frontiers in Optics 2007, San Jose, California United States Sep. 16, 2007 ISBN: 1-55752-846-2 From the session Biosensors I (FTuD) FTuD6.pdf.*
(Continued)

*Primary Examiner* — Yelena G Gakh
(74) *Attorney, Agent, or Firm* — Marianna Fuierer; Moore & Van Allen, PLLC

(57) ABSTRACT

The present invention provides for the surface plasmon-enhancement of long lived luminescent compounds, thereby providing for methods and systems having enhanced and controllable rates of the radiative emission of such relaxation of long lived luminescent compounds. The present invention achieves acceleration of the radiative processes by the interaction of the long lived luminescent compounds with surface plasmons of the metal surfaces.

6 Claims, 15 Drawing Sheets

Related U.S. Application Data

(60) Provisional application No. 60/950,492, filed on Jul. 18, 2007, provisional application No. 61/333,321, filed on May 11, 2010.

(51) Int. Cl.
*C09K 11/06* (2006.01)
*G01N 33/543* (2006.01)
*G01N 33/553* (2006.01)
*G01N 33/58* (2006.01)

(52) U.S. Cl.
CPC ..... *G01N 33/54373* (2013.01); *G01N 33/553* (2013.01); *G01N 33/582* (2013.01); *G01N 2458/30* (2013.01)

(58) Field of Classification Search
CPC ............ C12Q 2537/143; C12Q 1/6825; C12Q 1/6837; C12Q 2563/107; C12Q 2537/125; C12Q 1/66; C12Q 2535/122; C12Q 2561/113
See application file for complete search history.

(56) References Cited

U.S. PATENT DOCUMENTS

| | | |
|---|---|---|
| 7,400,397 B2 | 7/2008 | Lakowicz et al. |
| 7,566,783 B2 | 7/2009 | Lakowicz |
| 7,718,804 B2 | 5/2010 | Geddes et al. |
| 7,732,215 B2 | 6/2010 | Geddes et al. |
| 7,776,528 B2 | 8/2010 | Lakowicz |
| 7,939,333 B2 | 5/2011 | Geddes et al. |
| 7,989,220 B2 | 8/2011 | Lakowicz et al. |
| 8,008,067 B2 | 8/2011 | Geddes et al. |
| 8,027,039 B2 | 9/2011 | Lakowicz et al. |
| 8,034,633 B2 | 10/2011 | Geddes |
| 8,075,956 B2 | 12/2011 | Geddes et al. |
| 8,101,424 B2 | 1/2012 | Geddes |
| 8,114,598 B2 | 2/2012 | Geddes et al. |
| 8,182,878 B2 | 5/2012 | Geddes et al. |
| 8,318,087 B2 | 11/2012 | Geddes |
| 8,338,602 B2 | 12/2012 | Geddes et al. |
| 8,404,450 B2 | 3/2013 | Geddes et al. |
| 8,569,502 B2 | 10/2013 | Geddes et al. |
| 8,618,505 B2 | 12/2013 | Geddes |
| 8,679,402 B2 | 3/2014 | Geddes |
| 8,679,855 B2 | 3/2014 | Geddes |
| 8,722,428 B2 | 5/2014 | Geddes |
| 8,735,175 B2 | 5/2014 | Geddes |
| 8,759,110 B2 | 6/2014 | Geddes |
| 2003/0228682 A1 | 12/2003 | Lakowicz |
| 2006/0256331 A1 | 11/2006 | Geddes |
| 2007/0035724 A1 | 2/2007 | Banin et al. |
| 2007/0269826 A1 | 11/2007 | Geddes |
| 2008/0215122 A1 | 9/2008 | Geddes |
| 2009/0004461 A1 | 1/2009 | Geddes et al. |
| 2009/0022766 A1 | 1/2009 | Geddes |
| 2009/0325199 A1 | 12/2009 | Geddes |
| 2011/0020946 A1 | 1/2011 | Geddes |
| 2011/0207236 A1 | 8/2011 | Geddes |
| 2012/0021443 A1 | 1/2012 | Geddes |
| 2012/0028270 A1 | 2/2012 | Geddes |
| 2012/0107952 A1 | 5/2012 | Geddes |
| 2012/0282630 A1 | 11/2012 | Geddes |
| 2013/0115710 A1 | 5/2013 | Geddes |
| 2013/0156938 A1 | 6/2013 | Geddes |

OTHER PUBLICATIONS

Haushalter and Faris, "Strategy for photostable proximity bioassays using lanthanides", Appl. Opt., 2007, v. 46, No. 10, pp. 1918-1923.*
Kottman et al., Non-regularly shaped plasmon resonant nanoparticle as localized light source for near-field microscopy (J. Microscopy, 2001, v. 202, Pt. 1, pp. 60-65.*
Cubukcu et al., "Plasmonic Laser Antennas and Related Devices", IEEE J. Sel. Top. Quant. Electron., 2008, v. 14, No. 6, pp. 1448-1461.*
Yang et al. "Development of Polymer-Encapsulated Metal Nanoparticles as Surface-Enhanced Raman Scattering Probes" Small, 2009, v. 5, No. 2, pp. 198-202.*
Song et al. "Large Enhancement of Fluorescence Efficiency from CdSe/ZnS Quantum Dots Induced by Resonant Coupling to Spatially Controlled Surface Plasmons", NanoLetters, 2005, v. 5, No. 8, pp. 1557-1561.*
Rycenga et al. "Controlling the Synthesis and Assembly of Silver Nanostructures for Plasmonic Applications", Chem. Rev., 2011, v. 111, pp. 3669-3712.*
Aslan et al. "Fluorescent Core-Shell Ag@SiO2 Nanocomposites for Metal-Enhanced Fluorescence and Single Nanoparticle Sensing Platforms" J. Am. Chem. Soc., 2007, v. 129, pp. 1524-1525.*
Aroca, R. et al. Fluorescence Enhancement form Langmuir-Blodgett Monolayers or Silver Island Films, *Langmuir* (1988) 4, 518-521.
Aslan, K. et al. Metal-Enhanced fluorescence from silver nanoparticle-deposited polycarbonate substrates, *Journal of Materials Chemistry,* (2006), 16(27), 2846-2857.
Aslan K. et al. Metal-Enhanced Fluorescence from Gold Surfaces: Angular Dependent Emission, *J. Fluore.* (2007) 17, 7-13.
Aslan, K. et al. Metal-Enhanced Fluorescence from Plastic Substrates, *J. Fluo,* (2005) 15(2), 99-104.
Aslan, K. et al. Microwave-Accelerated Metal-Enhanced Fluorescence (MAMEF) with silver colloids in 96-well plates: Application to ultra fast and sensitive immunoassays, High Throughput Screening and drug discover, *J. Immuno Methods,* (2006) 312, 137-147.
Aslan, K. et al. Metal-Enhanced Fluorescence-Based RNA Sensing, *J. Am. Chem. Soc.,* (2006) 128, 4206-4207.
Aslan, K. et al. Directional Surface Plasmon Coupled Luminescence for Analytical Sensing Applications: Which Metal, What Wavelength, What Observation Angle? *Anal. Chem.* (2009) 81, 6913-6922.
Aslan, K. et al. Wavelength-Ratiometric Plasmon Light Scattering-Based Immunoassays, *Plasmonics* (2009)4(4), 267-272.
Aslan, K. et al. Metal-Enhanced chemiluminescence: advanced chemiluminescence concepts for the $21^{st}$ century, *Chem. Soc. Rev.* (2009), 38, 2556-2564.
Aslan, K. et al. Metal-Enhanced fluorescence: an emerging tool in biotechnology, *Current Opinion in Biotech.* (2005) 16: 55-62.
Aslan, K. et al. Metal-Enhanced Fluorescence Solution-Based Sensing Platform, *J. Fluore.* (2004), 14, 6, 677-679.
Aslan, K. et al Annealed Silver-Island Films for Applications in Metal-Enhanced Fluorescence: Interpretation in Terms of Radiating Plasmons, *J. Fluore,* (2005) 15, 643-654.
Barnes, W. L. Topical Review: Fluorescence near interfaces: the role of photonic mode density, *J. Modern Phys.* (1998) 45, 661-699.
Chen Y. et al. Dependence of Fluorescence Intensity of the Spectral Overlap between Fluorophores and Plasmon Resonant Single Silver Nanoparticles, *Nano Lett.* (2007) 7, 690-696.
Cheng D. et al. Separation distance dependent fluorescence enhancement of fluorescein isothiocyanate by silver nanoparticles, *Chem. Comm.* (2007), 248,248-250.
Chowdhury, M.H. et al. Metal-Enhanced chemiluminescence: Radiating plasmons generated chemically induced electronic excited states, *Appl. Phys. Lett.,* (2006) 88, 173104.
Dragan, A.I. et al. Voltage-Gated Metal-Enhanced Fluorescence II: Effects of Fluorophore Concentration on the Magnitude of Gated-Current, *J. Fluore.* (2009) 19(2), 369-374.
Fister, J.C. et al. Time-and Wavelength-Resolved Delayed-Fluorescence Emission from Acridine Yellow in an Inhomogeneous Saccharide Glass, *Anal. Chem.* (1996) 68, 639.
Fleming, G.R. et al. Picosecond Fluorescence Studies of Xanthene Dyes, *J. Am. Chem Soc.* (1977) 99, 4306-4311.
Geddes, C. D. Optical halide sensing using fluorescence quenching: theory, simulation and applications—a review, *Meas. Sci. Technol.* (2001) 12, R53-R88.
Geddes, C.D. et al. Metal-Enhanced Fluorescence, *J. Fluor.* (2002) 12, 121-129.

(56) References Cited

OTHER PUBLICATIONS

Glass, A.M. et al. Interaction of metal particles with adsorbed dye molecules: absorption and luminescence, *Opt. Lett.* (1980) 5, 368-370.
Isenberg, R. B. et al. Delayed Fluorescence in DNA-Acridine Dye Complexes, *PNAS*, 1964, 52(2), 379-387.
Jin Y.D. et al. Plasmonic fluorescent quantum dots, *Natu. nanotech.* (2009) 193-197.
Kaputskaya, I.A. et al. Spectral, kinetic and polarization characteristics of luminescence of acriflavine in polymetric matrix under pulsed excitation with different durations and insensities, *Chem. Phys.* (2006) 327, 171-179.
Kaputskaya, I.A. et al. The influence of Forster energy transfer on spectral and kinetic characteristics of phosphorescence and thermally activated delayed fluorscence of acriflavine in a polyvinylalcohol martrix, *J. Lumin.* (2006) 121, 75-87s.
Kawai, M. et al. Cell-wall thickness: possible mechanism of acriflavine resistance in meticillin-resistant *Staphylococcus aureus*, *J Med Microbiol;* (2009) 58 (3):331-336.
Kawai, M. et al. Mechanisms of action of acriflavine : electron micrscopic study of cell wall changes induced in *Staphylococcus aureus* by acriflavine, *Microbiol. Immuno.*, 2009, 53 (9) ,481.
Keyhani, E. et al. Acriflavine-Mediated Apoptosis and Necrosis in Yeast *Candida utilis*, *Acad Sci;* (2009) 1171, 284-291.
Kümmerlen J. et al. Enhanced dye fluorescence over silver island films: analysis of the distance dependence, *Mole. Phys*, (1993) 80, 1031-1046.
Lakowicz, J.R. Radiative decay engineering 5: metal-enhanced fluorescence and plasmon emission, *Anal. Biochem*, (2005) 337, 171-194.
Lakowicz, J.R. et al. Plasmon-controlled fluorescence: a new paradigm in fluorescence spectroscopy, *Analyst* (2008) 133, 1308-1346.
Lee, P.S. et al. Effects of Guanosine on the Pharmacokinetics of Acriflavine in Rats Following the Administration of a 1:1 Mixture of Acriflavine and Guanosine, a Potentional Antitumor Agent, *Arch Pharm Res.* (2007) 30, 372-380.
Lee, K. et al. Acriflavine inhibits HIF-1 dimerization, tumor growth and vascularization, *PNAS* (2009) 106:17910-17915.
Lim, E.C. et al. Delayed Fluorescence of Acriflavine in Rigid Media, *J. Chem. Phys.* (1962) 36, 118-122.
Llewellyn, B. D. et al. Nuclear staining with alum hematoxylin, *Biotechnic & Histochemistry* (2009) 84, 159-177.
Malicka, J. et al. Effects of fluorophore-to-silver distance on the emission of cyanine-dye-labeled oligonucleotides, *Analy. Bio.* (2003) 315, 57-66.
Misra, V. et al. Excitation energy transfer between acriflavine and rhodamine 6G as a pH sensor, *Sens. Actua. B.* (2000) 63, 18-23.
Misra, V. et al. An optical pH sensor based on excitation energy transfer in Nafion® film, *Sens. Actua.B:*, (2002) 82, 133-141.
Misra, V. et al. Effect of Polymer Microenvironment on Excitation Energy Migration and Transfer, *J. Phy Chem. B.* (2008) 112, 4213-4222.
Okamoto, K. et al. Surface-plasmon-enhanced light emitters based on InGaN quantum wells, *Nature Materials,* (2004) 3, 601-605.
Perkins, D. D. et al. Chromosome Rearrangements That Involve the Nucleolus Organizer Region in Neurospora, *Genetics* (1995) 141, 909-923.
Previte, M.J.R. et al. Surface plasmon coupled phosphorescence, *Chem. Phys. Lette.*, (2006) 432, 610-615.
Ray K. et al. Distance-Dependent Metal-Enhanced Fluorescence form Langmuir Blodgett Monolayers of Alkyl-NBD Derivatives on Silver Island Films, *Langmuir* (2006) 22, 8374-8378.
Ray, K. et al. Polyelectrolyte Layer-by-Layer Assembly to Control the Distance between Fluorophores and Plasmonic Nanostructures, *Chem. Mater.* (2007), 19, 5902-5909.
Ray, K. et al. Sulforhodamine Adsorbed Langmuir-Blodgett Layers on Silver Island Films: Effect of Probe Distance on the Metal-Enhanced Fluorescence, *J. Phys. Chem. C* (2007), 111, 7091-7097.
Sato, M., T. et al. Delayed Thermal Excimer Fluorescence of Acriflavine in a Stretched PVA Sheet, *Bull. Chem. Soc. Japan*, (1967) 40, 1031-1034.
Stoermer, R.L. et al. Distance-Dependent Emission from Dye-Labeled Oligonucleotide on Striped Au/Ag Nanowires: Effect of Secondary Structure and Hybridization, *J. Am Chem. Soc.* (2006) 128, 13243-13254.
Tarcha, P.J. et al. Surface-Enhanced Fluorescence on $SiO_2$ Coated Silver Island Films, *Appl. Spec.* (1999) 1, 53-58.
Tovmachenko, O. G. et al. Fluorescence Enhancement by Metal-Core/Silica-Shel Nanoparticles, *Adv. Mater.* (2006) 18, 91-95.
Wang, S. et al. Surface plasmon resonance enhanced optical absorption spectroscopy of studying molecular adsorbates, *Rev. Sci. Instr.* (2006) 72:7, 3055-3060.
Wu, M. et al. Enhanced Lanthanide Luminescence Using Silver Nanostructures: Opportunities for a New Class of Probes with Exceptional Spectral Characteristics, *J. Fluore.* (2005) 15:1, 53-59.
www.theinstitute of fluorescence.com\publications.
Zhang, Y. et al. Metal-Enhanced Phosphorescence: Interpretation in Terms of Triplet Coupled Radiating Plasmons, *J. Phys. Chem. B,* (2006) 110, 25108-25114.
Zhang, Y. et al. Metal-Enhanced e-type fluorescence, *Appl. Phys. Lett.*, (2008) 92, 013905.
Zhang, Y. et al. Voltage-Gated Metal-Enhanced Fluorescence, *J. Fluor.* (2009) 19, 363 367.
Zhang, Y. et al. Metal-Enhanced excimer (P-type) fluorescence, *Chem. Phys. Lett.* (2008) 458, 147-151.
Zhang, Y. et al. Metal-Enhanced phosphorescence, *Chem. Phys. Lette.*, (2006) 427, 432-437.
Zhang, Y. et al. Plasmonic engineering of singlet oxygen generation, *PNAS* (2008) 10:(6), 1798-1802.
Zhang, Y. et al. Wavelength Dependence of Metal-Enhanced Fluorescence, *J. Phys Chem. C.* (2009) 113, 12095-12100.
Zhang, J. et al. Enhanced Förster Resonance Energy Transfer on Single Metal Particle 2 Dependence on Donor—Acceptor Separation Distance, Particle Size, and Distance fron Metal Surface, *J. Phys. Chem. C* (2007), 111, 11784-11792.
Zhang, J. et al. Luminescent Silica Core/Silver Shell Encapsulated with Eu(III) Complex, *J. Phys. Chem. C* (2009) 113, 19404-19410.

* cited by examiner

TUNING OF METAL ENHANCED EMISSIONS OF LONG-LIVED LUMINESCENT COMPOUNDS

CROSS-REFERENCE TO RELATED APPLICATIONS

This application is filed under the provisions of 35 U.S.C. §371 and claims the priority of International Patent Application No. PCT/US2010/057946 filed on Nov. 24, 2010, which in turn claims priority to U.S. Provisional Patent Application No. 61/264,645 filed on Nov. 25, 2009, the contents of which are hereby incorporated by reference herein for all purposes, and is a Continuation-in-Part of U.S. patent application Ser. No. 12/016,247 filed on Jan. 18, 2008, now U.S. Pat. No. 9,023,372 which in turns claims priority to U.S. Provisional Application No. 60/950,492 filed on Jul. 18, 2007.

BACKGROUND OF THE INVENTION

Field of the Invention

The invention relates to emissions from long-lived luminescent compounds, and more particularly, to methods and systems for fine-tuning the emission yields and glow time of such compounds by coupling to surface plasmons of metallic particles.

Related Art

Fluorescence, phosphorescence and related technologies (herein referred to as "luminescence" to include in this context all processes where energy is emitted subsequent to an excitation process triggered by absorption of electromagnetic radiation) are now widely used in a variety of analytical schemes. Luminescent materials are used as tracers on the basis of the high detection sensitivity that can be achieved, but are also used as environmentally responsive "probes" to monitor local conditions, such as pH, ion concentrations, oxygen tension etc. Luminescent compounds can also be used to detect and sometimes quantify the proximity of an agent which is able to modify the emission process on close approach or contact.

In recent years, there has been growing interest in understanding the interactions of fluorophores with metallic particles [1, 2]. Spectral properties of fluorophores are found to be dramatically changed near particulate surfaces due to surface plasmon interactions. A huge enhancement in fluorescence intensity along with an increased absorption, a decrease in decay times and an increase in photo-stabilities and angular-dependent emission are also frequently observed [3, 4]. The phenomenon subsequently been named as metal-enhanced fluorescence (MEF) by Geddes [3]. The current interpretation of MEF has been underpinned by a radiating plasmon model (RPM) [5], whereby non-radiative energy transfer occurs from excited fluorophores to surface plasmons in non-continuous films due to fluorophore-plasmon near field coupling. The surface plasmons efficiently radiate the emission of the coupling fluorophores. Studies have been conducted to show increased detectability [6] and photostability of fluorophores [7], chemiluminescent compounds [8] and improved DNA detection [9], drug discovery and high-throughput screening [10] immunoassays [11], singlet oxygen generation [12] etc. to name but just a few.

Phosphorescent compounds, considered to be long-lived luminescent compounds, have the ability to store light and then slowly release such light energy. Phosphorescent compounds can move from the ground state (singlet state) to a metastable (triplet state) and slowly decay back to the ground state. Thus, a phosphorescent compound can emit light ever after the excitation source is removed. However, the intensity of the emission can be greatly reduced because of this slow release of energy.

A fluorescent compound glows under the excitation of an energy source and as soon as the energy source is removed, the compound stops emitting light. However, long-lived fluorescence molecules are different, in that, such compounds show a delayed fluorescence ($\alpha$-$S_1$-$3S_0$) and phosphorescence ($T_1 \rightarrow S_0$) at room temperature along with traditional fluorescence ($S_1$-*So). This type of long lived fluorescence i.e. delayed fluorescence arises due to different mechanisms [24]. The population of the excited singlet state ($S_i$) by thermal activation of the triplet state ($T_i$) is responsible for E type delayed fluorescence, whereas a triplet-triplet annihilation process gives rise to P-type delayed fluorescence. The third type of delayed fluorescence is attributed to the recombination of radial ions and matrix trapped electrons produced by photoionization of the molecules. Because of its long decay time, delayed fluorescence has been widely used to investigate the rotational diffusion time of biological macromolecules in membranes and also used to characterized metal oxide surfaces [12].

However, because of the delayed emissions and lower intensity of such emissions, many important luminescent compounds are not used as high flux luminescent materials. As such, it would be advantageous to provide for systems and methods that can provide for shorter lived and brighter higher photon flux luminescent materials.

SUMMARY OF THE INVENTION

The present invention provides for surface plasmon-enhancement of long lived luminescent compounds, thereby providing for methods and systems having enhanced and controllable rates of the radiative emission of such relaxation of long lived luminescent compounds. The present invention achieves acceleration of the radiative processes by the interaction of the long lived luminescent compounds with surface plasmons of the metal surfaces.

Specifically, the present invention provides for accelerating the radiative decay and enhanced intensity of emissions of long-lived luminescent compounds, including delayed fluorescent compounds and phosphorescent compounds by interaction with surface plasmons in metal nanostructures and surfaces. Interaction between surface plasmons and the light emitting compounds is achieved by bringing them into close proximity and providing a mechanism for their efficient interaction. Coupling of surface plasmons to the light emitting molecules can be performed by using special coupling devices, binding ligands or any method for providing spatial interaction. In order for the acceleration of the radiative decay and increase intensity of emission of the long lived luminescent compounds to occur, the metal surface is spatially separated from the light emitting compounds by about 0.1 nm to 40 nm, and more preferably from about 1 nm to about 20 nm, and most preferably from about 1 nm to about 5 nm.

In one aspect, the present invention provides for a method for increasing radiative decay and/or increased emission intensity, the method comprising:
  a) providing a surface substrate, wherein at least a section of the substrate is coated with a metallic material that exhibits surface plasmons on excitation;
  b) coupling a long lived luminescent compound to the metallic material by a linker, attachment to a surface coating covering the metallic material or impregnated into the surface coating and wherein the long lived luminescent compound is positioned at a distance from the metallic material that provides for coupling interaction between the long lived luminescent compounds long lived luminescent compound and excited metallic surface plasmons; and c) irradiating the long lived luminescent compound in an amount sufficient to excite the long lived luminescent compound causing an interaction with the surface plasmons of the metallic material.

The metallic material is preferably a metal that exhibits surface plasmons including silver, gold, copper, aluminum, zinc, nickel, palladium, tungsten, platinum, germanium, indium, iron, tin, rhodium and combinations thereof.

The metallic material may take the form of multiple structures, such as, metallic islands, nanostructures, colloids, porous matrix, metallic particles impregnated within a glass or polymeric surface and/or a metallic surface in a patterned shape.

The patterned shape of metallic structures has at least apex, with cross-sections of the structures selected from, but not limited to a triangle, square, rectangle, trapezoid, polygon, elliptical, oblong or combinations thereof. Further, emissions and reactivity can be enhanced by placement of metallic structures having a shape with an apex area and positioning such apex areas adjacent to each other and creating a reactive zone therebetween. The metallic structures when fabricated into geometric shapes comprising an apex area for forming a reactive zone can be positioned on assay system with multiple wells wherein the reactive zone includes the wells. The distance between the apex areas may range from 0.01 mm to 5 mm, more preferably from 2 mm to about 3 mm and depending on the size of the required reactive zone. The thickness of the metallic geometric shaped forms ranges from 25 nm to about 1000 nm, and more preferably from about 45 nm to about 250 nm.

The metallic structures may include a combination of metals, deposited in any order on a substrate, for example silver, gold, or gold and then a silver layer. Further the metallic structures can be in particulate form in solution. The forms can be in a nanoball shape with an internal metal core, a silica or oxide layer and another top metallic layer wherein the core metal is different from the outer layer. In the alternative, both the core and outer layers can be fabricated of a mixed-metal combination.

The surface substrate may be fabricated of a polymeric material, glass, paper, nitrocellulose, combinations thereof or any material that provides sufficient stability for placement of the metallic structures.

In another aspect, the present invention relates to a method for increasing radiative decay and/or increased emission intensity, the method comprising:

a) providing a metallic core with a surface coating, wherein the metallic core exhibits surface plasmons on excitation;

b) coupling a long-lived luminescent compound to the metallic core, wherein the long-lived luminescent compound is attached to a surface coating covering the metallic core or impregnated into the surface coating and wherein the long-lived luminescent compound is positioned at a distance from the metallic core to provide for coupling interaction between the long-lived luminescent compound and metallic surface plasmons; and c) irradiating the long lived luminescent compound in an amount sufficient to excite the long lived luminescent compounds causing an interaction with the surface plasmons of the metallic core and increasing radiative decay.

The coating can be evenly distributed on the metallic core, in a pattern, or discontinuously distributed and having a thickness from about 0.5 nm to about 125 nm. The metallic core can be a solid metallic sphere or a core of one material that is coated with a metallic surface. Preferably the metallic sphere has a diameter ranging from about from about 2 nm to 150 nm and more preferably from about 20 to 100 nm. The metallic core may be fabricated from any metal described herein above. Further the long-lived luminescent compounds may be evenly distributed, randomly or patterned within or on the coating encompassing the metallic core.

In a still further aspect the present invention provides for a long-lived luminescent compound complex comprising:

a) a surface substrate, wherein at least a section of the substrate is coated with a metallic material that exhibits surface plasmons on excitation; and b) a long-lived luminescent compound coupled to the metallic material, wherein the long-lived luminescent compound is positioned at a distance from the metallic material to provide for coupling interaction between the long-lived luminescent compound and metallic surface plasmons and at a distance from about 0.1 nm to about 40 nm.

In another aspect, the long-lived luminescent compound complex of the present invention may also be conjugated with at least one targeting moiety, attached to the surface coating, surface substrate or metallic material depending on the fabrication of the complex, wherein the targeting moiety is specific for a cancer- and/or pathogen-specific marker on a tumor. The targeting moiety may include but is not limited to an antibody or fragment thereof, a protein or a fragment thereof, an antisense nucleic acid, a polypeptide, a peptide nucleic acid, or an oligonucleotide. Thus, upon administration to a subject, the long-lived luminescent compound complex will specifically bind to those cells and/or organisms that express the biological entity specific for the targeting moiety. The subject is then exposed to electromagnetic radiation at a frequency for absorption by the attached long-lived luminescent compounds to be used for emitting radiation. The target moiety may be attached to the surface coating through a linker, wherein the linker attaches the targeting moiety to the coating may include a lipid, a carbohydrate, a polysaccharide, a protein, a polymer, a glycoprotein, or a glycolipid.

Yet another aspect of the present invention provides a long-lived luminescent compound complex comprising;

a) a metallic core with a surface coating, wherein the metallic core exhibits surface plasmons on excitation; and b) long-lived luminescent compounds coupled to the metallic core, wherein the long-lived luminescent compounds compound are attached to a surface coating covering the metallic core or impregnated into the surface coating and wherein the long-lived luminescent compounds are positioned at a distance from the metallic core to provide for coupling interaction between the long-lived luminescent compounds and excited metallic surface plasmons and at a distance from about 0.1 nm to about 40 nm.

A further aspect of the present invention provides for a detection system, the system comprising:

a) a substrate comprising a multiplicity of metallic structures, wherein the metallic structures comprise a single metal, a combination of metals in layers or in a mixture;

b) long-lived luminescent compounds positioned near the metallic structure material in a range from about 0.1 nm to 40 nm, wherein the long-lived luminescent compounds are selected from the group of a phosphorescent compounds, delay fluorescent compounds and alpha fluorescent compounds;

c) a source of electromagnetic energy for providing excitation energy to excite the long-lived luminescent compounds; and d) a detector for detecting emissions from the excited molecule and/or the metallic structure.

In yet another aspect, the present invention relates to a method for detecting a target molecule in a sample, the method comprising:

a) providing a system comprising:
   a layer of immobilized metallic structures comprising mixed metal, wherein the immobilized metallic structures have attached thereto a captured biomolecular probe with an affinity for the target molecule; and
   a free biomolecular probe with an affinity for the target molecule, wherein the free biomolecular probe has attached thereto a long-lived luminescent compound;

b) contacting the sample with the immobilized biomolecular probes, wherein the target molecules in the sample bind to the immobilized biomolecular probes; and c) contacting the bound target molecule with the free biomolecular probe, wherein binding of the free biomolecular probe to the target molecule causes the long-lived luminescent compound to be positioned a sufficient distance from the immobilized metallic structures to enhance radiative decay and emission intensity of the long-lived luminescent compounds.

The substrate positioned beneath the metallic structures may include glass, quartz, plastics (such as on the bottom of HTS plates, polystyrene, polycarbonate), semiconductors, paper, cellulose, cotton, nylon, silk, sapphire, diamond, ruby, dielectric materials such as polystyrene etc.

The metallic structures may include an oxide layer, positioned between two metal layers. The oxide layer coating may include at least one metal selected from the group consisting of Al, Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $Al_2O_3$, $SiO_2$, $TiO_2$, $Fe_2O_3$, $CuO$, $ZnO$, $Y_2O_3$, $ZrO_2$, $Nb_2O_5$, $MoO_3$, $In_2O_3$, $SnO_2$, $Sb_2O_5$, $Ta_2O_5$, $WO_3$, $PbO$ or $Bi_2O_3$. These metal oxides may be used alone or in combination with other types of coatings. Preferably, the oxide is a silicon oxide, more preferably, $SiO_2$.

In yet another aspect, the present invention provides a method for detecting a targeted pathogen in a sample, the method comprising:

a) providing a system comprising:
   1. an immobilized metallic material positioned on a surface substrate, wherein the immobilized metallic material has attached thereto an immobilized capture DNA sequence probe complementary to a known DNA sequence of the target pathogen; and
   2. a free capture DNA sequence probe complementary to a known DNA sequence of the target pathogen, wherein the free capture DNA sequence probe has attached thereto a long-lived luminescent compound;

b) contacting the sample with the immobilized capture DNA sequence probe, wherein the DNA sequence of the target pathogen binds to the immobilized capture DNA sequence probe;

c) contacting the bound DNA sequence of the target pathogen with the free capture DNA sequence probe, wherein binding of the free capture DNA sequence probe to the DNA sequence of the target pathogen causes the long-lived luminescent compound to be positioned a sufficient distance from the immobilized metallic material to enhance fluorescence emission; and d) irradiating the system with electromagnetic energy in a range from UV to IR to increase fluorescence emission by the long-lived luminescent compound.

Another aspect of the present invention relates to a bioassay for measuring concentration of receptor-ligand binding in a test sample, the method comprising:

a) preparing metallic nanostructures of the present invention immobilized on a surface wherein the metallic nanostructures have positioned thereon a receptor molecule having affinity for a ligand of interest;

b) contacting the receptor molecule with the test sample suspected of comprising the ligand of interest, wherein the ligand of interest will bind to the receptor molecule to form a receptor-ligand complex;

c) contacting the receptor-ligand complex with a detector molecule having affinity for the ligand to form a receptor-ligand-detector complex, wherein the detector molecule comprises a long-live luminescent compound and positioned about 0.1 nm to about 40 nm from the metallic structures; and d) exposing the receptor-ligand-detector complex to excitation energy for excitation of the long-lived luminescent compound and measuring the intensity of radiation emitted from exited metallic surface plasmons and/or test sample.

A further aspect of the present invention, relates to a kit for detecting a target molecule in a sample, the kit comprising a) a container comprising a layer of immobilized metal particles deposited on a substrate surface wherein an immobilized probe is connected to the metal particles and wherein the immobilized probe has an affinity for the target molecule;

b) a long-lived luminescent compound having an affinity for the target molecule, wherein the binding of the target molecule to both the immobilized probe and long-lived luminescent compound causes the long-lived luminescent compound to be positioned a sufficient distance from the immobilized metal particles to enhance fluorescence emission; and c) a source of energy to excite the long-lived luminescent compound causing an interaction between the long-lived luminescent compounds and surface plasmons of the metal particles.

In another aspect the present invention relates to a system for generating electrical current, the system comprising:

1. a substrate comprising a plurality of metallic structures, wherein the metallic structures are at least partially covered with a polar solution;

2. a set of electrodes communicatively contacting at least some of the metallic structures positioned thereon;

3. long-lived luminescent compounds positioned near the metallic structures and at a distance from about 0.1 nm to about 40 nm from the metallic structures, wherein when the long-lived luminescent compounds is excited by electromagnetic energy a mirror dipole is induced in the metal structures causing plasmonic current flow for storage, directing to a current reading device or to provide sufficient amperage to power a device.

Importantly, the current is increased as the amount of long-lived luminescent compounds increases, thereby providing for an assay that provides an electrical signal proportional to the amount of binding of excitable probes, that being the long-lived luminescent compounds to target substances.

The method and system described above may be used in multiple detecting systems, including but not limited to, immunoassays, hybridization assays, resonance energy transfer assays, polarization/anisotropy based assays, luminescence based assays, and enzyme-linked immunosorbent assays.

Other features and advantages of the invention will be apparent from the following detailed description, drawings and claims

DETAIL DESCRIPTION OF THE INVENTION

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, peptides, lipids, antibodies and phycobiliproptein.

The term "receptor-ligand" as used herein means any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, or infection to be assayed.

Figure 1:
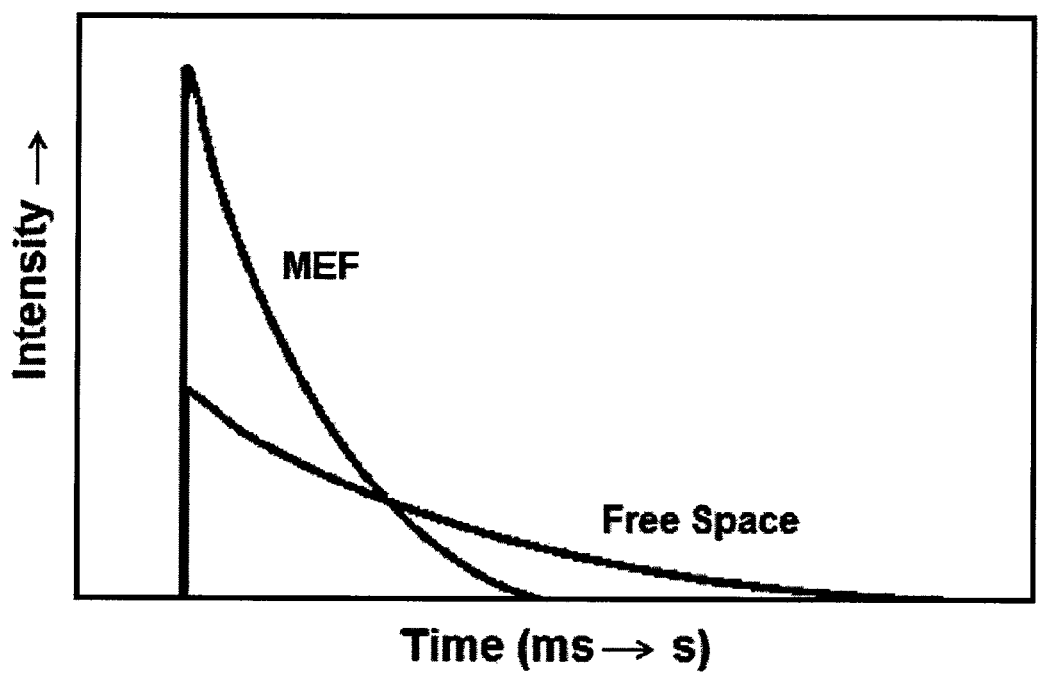
FIG. 1 illustrates the MEF effect for long lived luminescent compounds. The intensity increases along with a shorter decay time as compared to the free space condition

The photo-physical properties of long lived luminescent compounds are found to be both drastically and favorably changed near the metallic nano particle surfaces in such a ways that an opportunity for the development of shorter lived brighter higher photon flux luminescent materials can be realized. FIG. 1 in the attached set of figures, shows that a typical phosphor material in the normal free space condition, decays over a long time period, with a low and decaying emission intensity (i.e. brightness). However, in the presence of plasmon resonant particles, the total brightness (glow) of the material, is substantially increased, and the glow time reduced. This coupling of both the ground-state and excited state of the phosphor's to the plasmon resonant particles allows for the glow time and brightness to be tuned to make new hybrid materials.

Representative long-lived luminescent compounds include, but are not limited to, any phosphor which includes phosphorescent, alpha-fluorescent or delay fluorescent compounds. A long-lived luminescent compound generally has a luminescence lifetime equal to or more than 1 microsecond (the lifetime being calculated as the time wherein luminescence emission intensity decays to the relative value of 1/e, i.e. to approximately 37% of the original luminescence emission intensity). The compounds capable of long-lived luminescence include, but are not limited to, lanthanide chelates, lanthanide-chelate dyed-nanoparticles, lanthanide phosphors and nanophosphors, porphyrins, and porphyrin dyed-nanoparticles.

Phosphor compounds may also include, but are not limited to $Zn_2SiO_4$:Mn (Willemite); ZnS:Ag+(Zn,Cd)S:Ag; ZnS:Ag+ZnS:Cu+$Y_2O_2$S:Eu; ZnO:Zn; ZnS:Ag,Cl; ZnS:Zn; (KF,$MgF_2$):Mn; (Zn,Cd)S:Ag; (Zn,Cd)S:Cu; $Y_2O_2$S:Eu+ $Fe_2O_3$, ZnS:Cu,Al; ZnS:Ag+Co-on-$Al_2O_3$; (KF,$MgF_2$):Mn; (Zn,Cd)S:Cu,Cl; ZnS:Cu; ZnS:Cu,Ag; $MgF_2$:Mn; (Zn,Mg)$F_2$:Mn; $Zn_2SiO_4$:Mn,As; ZnS:Ag+(Zn,Cd)S:Cu; $Gd_2O_2$S: Tb; $Y_2O_2$S:Tb; $Y_3Al_5O_{12}$:Ce; $Y_2SiO_5$:Ce; $Y_3Al_5O_{12}$:Tb; ZnS:Ag,Al; ZnS:Ag; ZnS:Cu,Al; ZnS:Cu,Au,Al; (Zn,Cd)S: Cu,Cl+(Zn,Cd)S:Ag,Cl; $Y_2SiO_5$:Tb; $Y_2OS$:Tb; $Y_3$ (Al,Ga)$_5O_{12}$:Ce, $Y_3$(Al,Ga)$_5O_{12}$: Tb, $InBO_3$:Tb, $InBO_3$: Eu, $InBO_3$:Tb+$InBO_3$:Eu, $InBO_3$:Tb+$InBO_3$:Eu+ZnS:Ag, (Ba,Eu)$Mg_2Al_{16}O_{27}$, (Ce,Tb)$MgAl_{11}O_{19}$, $BaMgAl_{10}O_{17}$: Eu,Mn, $BaMg_2Al_{16}O_{27}$:Eu(II), $BaMgAl_{10}O_{17}$:Eu,Mn, $BaMg_2Al_{16}O_{27}$:Eu(II),Mn(II), $Ce_{0.67}Tb_{0.33}MgAl_{11}O_{19}$:Ce, Tb, $Zn_2SiO_4$:Mn,$Sb_2O_3$, $CaSiO_3$:Pb,Mn, $CaWO_4$ (Scheelite), $CaWO_4$:Pb, $MgWO_4$, (Sr,Eu,Ba,Ca)$_5$(PO$_4$)$_3$Cl, $Sr_5$Cl (PO$_4$)$_3$:Eu(II), (Ca, Sr,Ba)$_3$(PO$_4$)$_2$Cl$_2$:Eu, (Sr,Ca,Ba)$_{10}$(PO$_4$)$_6$Cl$_2$:Eu, $Sr_2P_2O_7$:Sn(II), $Sr_6P_5BO_{20}$:Eu, $Ca_5$F(PO$_4$)$_3$: Sb, (Ba,Ti)$_2P_2O_7$:Ti, $3Sr_3$(PO$_4$)$_2$.$SrF_2$:Sb,Mn; $Sr_5$F(PO$_4$)$_3$: Sb,Mn; $Sr_5$F(PO$_4$)$_3$:Sb,Mn; $LaPO_4$:Ce,Tb; (La,Ce,Tb)PO$_4$, (La,Ce,Tb)PO$_4$:Ce,Tb; $Ca_3$(PO$_4$)$_2$.$CaF_2$:Ce,Mn; (Ca,Zn, Mg)$_3$(PO$_4$)$_2$: Sn; (Zn, Sr)$_3$(PO$_4$)$_2$:Mn; (Sr,Mg)$_3$(PO$_4$)$_2$: Sn; (Sr,Mg)$_3$ (PO$_4$)$_2$: Sn(II); $Ca_5$F(PO$_4$)$_3$: Sb,Mn; $Ca_5$(F,Cl) (PO$_4$)$_3$: Sb,Mn; (Y,Eu)$_2O_3$, $Y_2O_3$:Eu(III); $Mg_4$(F)GeO$_6$:Mn; $Mg_4$(F)(Ge,Sn)O$_6$:Mn; Y(P,V)O$_4$:Eu; YVO$_4$:Eu; $Y_2O_2$S:Eu; 3.5MgO0.5 $MgF_2$ $GeO_2$Mn; $Mg_5As_2O_{11}$:Mn; $SrAl_2O_7$:Pb; $LaMgAl_{11}O_{19}$:Cc; $LaPO_4$:Ce; $SrAl_{12}O_{19}$:Ce; $BaSi_2O_5$:Pb; $SrFB_2O_3$:Eu(II); $SrB_4O_7$:Eu; $Sr_2MgSi_2O_7$:Pb and $MgGa_2O_4$:Mn(II).

Delayed fluorescent compounds are defined by compounds that exhibited three different types of delay emissions, including; E-type delayed fluorescence wherein the first excited singlet state becomes populated by a thermally activated radiationless transition from the first excited triplet state; P-type delayed fluorescence wherein the first excited singlet state is populated by interaction of two molecules in the triplet state (triplet-triplet annihilation) thus producing one molecule in the excited singlet state; and Recombination fluorescence wherein the first excited singlet state becomes populated by recombination of radical ions with electrons or by recombination of radical ions of opposite charge. Numerous organic materials exhibit delayed fluorescence including, but limited to acetophenone, phenanthrene, acridine type compounds such acridine orange, eosin, acriflavine, anthracene, naphthaline, acenaphthene, fluoranthene, 1:2-benzanthracene pyrene, 3:4-benzpyrene, fullerene, porphyrin compounds, proflavine, benzoflavine, thioflavine, 8-aza-D-homogonane, and 1-chloronaphthalene.

Surface plasmons are collective oscillations of free electrons at metallic surfaces. When a metallic article or surface is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this re-radiation of light at the same incident wavelength that is often referred to as plasmon emission. In the present invention electromagnetically induced electronic excited states caused by exciting a long-lived luminescent compounds couple to surface plasmons to produce emission intensities greater than from about 5 to 1000-fold, as compared to a control sample containing no metallic surface.

The emission enhancement may be observed at distances according to the type of long-lived luminescent compounds to be detected and the type, shape of the metal material, noting a difference between a film and a metallic island or colloid. For example, emission enhancement may be observed when a long-lived luminescent compounds is distanced about 0.1 nm to about 40 nm to metal surfaces. Preferable distances are about 1 nm to about 20 nm, and more preferably, 1 nm to about 5 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Attachment of the long-lived luminescent compounds to a probe may be achieved by any of the techniques familiar to those skilled in the art. For example, the long-lived luminescent compounds may be covalently attached to the bimolecular probe by methods disclosed in U.S. Pat. No. 5,194,300 Cheung and U.S. Pat. No. 4,774,189 Schwartz.

The assay system of the present invention provides for detecting and separating at least two target pathogen by choosing long-lived luminescent compounds such that they possess substantially different emission spectra, preferably having emission maxima separated by greater than 10 nm, more preferably having emission maxima separated by greater than 25 nm, even more preferably separated by greater than 50 nm. When differentiation between the two long-lived luminescent compounds is accomplished by visual inspection, the two dyes preferably have emission wavelengths of perceptibly different colors to enhance visual discrimination. When it is desirable to differentiate between the two long-lived luminescent compounds using instrumental methods, a variety of filters and diffraction gratings allow the respective emission maxima to be independently detected.

The present invention provides enhanced emissions using metallic structures of elliptical, spherical, triangular, rod-like forms or any geometric form. In exemplary cases, the elliptical islands have aspect ratios of 3/2, and the spherical colloids have diameters of 20-60 nm. Using known coating techniques, the placement of metallic structures could be controlled precisely, as close as 50 nm apart.

Further, the metallic structures can be fabricated to form a geometric shape with a cross-section such as triangle, square, oblong, elliptical, rectangle, or any shape that provides at least apex area of the metallic surface. It is envisioned that the apex area includes not only pointed regions but regions with rounded edges such as found in an oblong or elliptical shape. The apex areas are preferably arranged so that one apex area is opposite from another apex area and aligned to cause the reactive zone to be positioned therebetween. The distances between the apex areas may range from 0.01 mm to 5 mm, more preferably from 2 mm to about 3 mm and depending on the size of the required reactive zone. The thickness of the metallic geometric shaped forms ranges from 25 nm to about 1000 nm, and more preferably from about 45 nm to about 250 nm.

The metallic material may, alternatively, be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which compounds will flow and be both detected and counted more efficiently.

The emission induction of a mirror dipole from the excited molecule to the metallic structure may be observed at distances according to the type of excitable molecule to be detected and the type of metal. For example, induction of a current may be observed when a long-lived luminescent compounds is positioned from about 0.1 nm to about 40 nm to metal surfaces. Preferable distances are about 1 nm to about 20 nm. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Preparation of Silver Metal Islands

The island particles are prepared in clean beakers by reduction of metal ions using various reducing agents. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Alternative procedures for preparing metal particles are also available. Silver is primarily used because of the familiar color from the longer surface plasmon absorption of silver.

Preparation of Silver Colloids

Colloids can be prepared as suspensions by citrate reduction metals. Preferred metals are silver and gold. Again, gold may be because of the absorption of gold at shorter wavelengths. However, gold colloids may be used with longer wavelength red and NIR fluorophores.

The size of the colloids and their homogeneity can be determined by the extensive publications on the optical properties of metal particles available and the effects of interface chemistry on the optical property of colloids.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.

Metallic colloids (or various other non-spherical shapes/particles) may also be incorporated into organic polymers, covalently or non-covalently, to form polymeric matrices, wherein the distance from diffusing compounds affords an increase in radiative decay rate and thus, an increase in quantum yield. Such polymeric matrices are ideal for sensing/flowing sensing applications of low concentration compounds.

When the aspects of the present invention are used in the method of generating plasmonic electricity, the electrode system of the present invention may include a containment vessel that includes two electrodes, anode and cathode, attached to the vessel, communicatively connected to the metallic structures or the electrode can be inserted into solution. Generally the electrodes can be fabricated from any conductive metal and may include carbons, noble metals or alloys of Pt, Pd, Ir, Au, Ru, etc., noble metals or alloys deposited on a substrate such as Ti or Ta. Metals and metal alloys are preferred having a conductivity of greater than about $10^{-4}$ S/cm. In the alternative, wire electrodes can be directly attached to two of the metallic particles, wherein the metallic particles and attached wires are separated sufficiently to detect optimal current flow.

Further, the electrodes can be fabricated from any electrically conducting polymer, electrically conducting ceramic, electrically conducting glass, or combinations thereof including metal oxides and selected from tin, lead, vanadium, titanium, ruthenium, tantalum, rhodium, osmium, iridium, iron, cobalt, nickel, copper, molybdenum, niobium, chromium, manganese, lanthanum, or lanthanum series metals or alloys or combinations thereof, and possibly containing additives like calcium to increase electrical conductivity.

Electrolytes in an aqueous solution or polar solvents may include an ionically conductive aqueous or non-aqueous solution or material, which enhances the movement of current between electrodes. The electrolyte may include NaCl, KCl, $NH_4Cl$, NaI, KI, NaAc, NaOH, $AgNO_3$, $CuSO_4$, $LiClO_4$, $NaClO_4$, $KClO_4$, $AgClO_4$, $NaBrO_4$, etc. The polar solvents may include water, ethanol, and methanol.

The present invention further comprises a detection device for detecting emissions including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, fluorescence correlation spectroscopy, scanning microscopes, confocal microscopes, capillary electrophoresis detectors, or other light detector capable of detecting the presence, location, intensity, excitation and emission spectra, fluorescence polarization, fluorescence lifetime, and other physical properties of the luminescent signal.

Excitation light sources can include arc lamps and lasers, natural sunlight, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a long-lived luminescent compounds absorbs two photons simultaneously, it will absorb enough energy to be raised to an excited state. The long-lived luminescent compounds will then emit a single photon with a wavelength that depends on the long-lived luminescent compounds used and typically in the visible spectra. The use of the Ti-sapphire laser with infrared light has an added benefit, that being, longer wavelengths are scattered less, which is a benefit to high-resolution imaging. Importantly, there is reduced background signal level gained by using 2-photon excitation as compared to 1-photon excitation by utilizing localized excitation near by a metallic particles.

In one embodiment, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic structures, which is contrary to most metal objects, such as that recognized by placing a spoon in a microwave oven.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether. For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur. However, as discuss hereinbelow, the charge carriers which are displaced by the electric field are subject to resistance in the medium in which they travel due to collisions with the lattice phonons. This leads to Ohmic heating of the metallic structures in addition to the heating of any surface polar molecules. Intuitively, this leads to localized heating around the metallic structures in addition to the solvent, rapidly accelerating assay kinetics.

In the present invention, microwave radiation may be provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite fluorescing molecules. The light can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

There are many important assays that can directly benefit from enhanced signal intensities and quicker kinetics. For example, myoglobin concentrations for heart attack patients, patients of toxic shock and pancreatitus. All of these assays are widely used in hospitals emergency rooms with assay times of greater than 30 minutes. Thus, the present invention can be used for points-of-care clinical assessment in emergency rooms.

An alternative method of increasing the speed of any chemical or biochemical reaction may be effected by using any device capable of generating and transmitting acoustic energy through any medium to transit ultrasonic atomizing energy. The ultrasonic emitting device can be placed in either the interior of a vessel used in a detection system or positioned adjacent thereto for transmitting energy into the vessel. The device may include components for the traditional electromagnetic stimulation of piezoelectric transducers, (man-made or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to ($R_1$: $R_2$). Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

In one embodiment, the present invention relates to a metallic particle, such as a metallic sphere or core encompassed with a polymer or silica coating for positioning of a long-lived luminescent compounds and wherein the long-lived luminescent compounds are directly attached to the coating or impregnated within the coating. The coating can be evenly distributed on the metallic core, continuously, in a pattern, or discontinuously distributed. The metallic core can be any shape including sphere, rod, elliptical and can be a solid metallic core or a core of another material that is coated with a metallic surface. Preferably the metallic core has a diameter ranging from about from about 2 nm to 150 nm and more preferably from about 20 to 100 nm.

The thickness of the coating is generally the thickness to provide a distance wherein the long-lived luminescent compounds is from about 0.1 nm to about 40 nm from the metal surfaces to provide optimal enhancement of triplet yield. Preferable distances are about 1 nm to about 20 nm depending on placement of the long-lived luminescent compounds including the use of a linker or whether it is impregnated into the coating. Thus, the thickness of the coating can be from about 0.1 nm to about 40 nm.

The metallic core of the nanospheres or the metallic structures of the present invention may be coated with a synthetic or naturally occurring polymer. Exemplary polymers useful in the present disclosure include, but are not limited to, polyesters, polyamides, polyethers, polythioethers, polyureas, polycarbonates, polycarbamides, proteins, polysaccharides, polyaryls, polyvinyl alcohol, etc. The polymers useful in the coatings may include average molecular weights ranging from 100 g/mol to 100,000 g/mol, preferably 500 g/mol to 80,000 g/mol. Notably, the polymer may be a biodegradable polymer such as synthesized from monomers selected from the group consisting of D, L-lactide, D-lactide, L-lactide, D, L-lactic acid, D-lactic acid, L-lactic acid, glycolide, glycolic acid, hydroxybutyric acids, and malic acid.

In another embodiment the surface coating may be formed from an oxide containing compound or include an oxide containing compound. The oxide layer may be formed from a deposition technique, such as vapor deposition. The oxide layer coating may include at least one metal selected from the group consisting of Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $SiO_2$, $TiO_2$, $Fe_2O_3$, CuO, ZnO, $Y_2O_3$, $ZrO_2$, $Nb_2O_5$, $MoO_3$, $In_2O_3$, $SnO_2$, $Sb_2O_5$, $Ta_2O_5$, $WO_3$, PbO or $Bi_2O_3$. These metal oxides may be used alone or in combination with other types of coatings. Preferably, the oxide is a silicon oxide, more preferably, $SiO_2$. The vapor deposition of $SiO_2$ is a well established technique for the controlled deposition of a variety of substrates. For example, an Edwards Vapor deposition module allows the deposition of an inert coating of $SiO_2$.

Method for fabrication of the metallic sphere is fully disclosed in copending application U.S. patent Ser. No. 12/016,247 entitled "METAL-ENHANCED FLUORESCENCE NANOPARTICLES," the content incorporated by reference herein for all purposes.

Potential applications of the present invention using the long-lived luminescent compounds that provide the advantages of eliminating the need to re-excite the materials after initial excitation while still having emissions after excitation ceases, include the following:

To increase the photostability, brightness and dwell time in microscopy and imaging technologies;

On fabrics, textiles and garments for improved visualization, such as safety wear for road side workers or on jogging wear for visualization by traffic, For Safety lighting, strips; road signs; emergency exit signs;

In cosmetics to change the brightness of skin and hair products and to allow the reduced concentration of dyes/pigments in the formulations;

In paints, coatings and inks to enhance brightness as well as protect the material substrates against sun damage;

In Televisions, LCD and plasma screen to both increase brightness and yet also alter the spatial distribution of luminescence (fluorescence, phosphorescence, etc);

Coated in or on Light Emitting Diodes to increase brightness and the spatial distribution of the emitted light;

In bank notes, stock certificates etc as an anti-counterfeiting technology. The angular nature and enhanced luminescence signatures can not be simply duplicated by simple printing or photocopying;

In light bulbs, strip lights, torches, car head lights etc (any type), to enhance the light throughput and modify as needed the spatial distribution of the light, coating on the outside of light bulbs or LEDs for after lighting after the bulb is turned off, and as night light devices, which are powered by day or room light.

On and with fiber optics and optical cables to enhance luminescence signatures, increase the extent of light coupling into the fiber as well as increase and tune the extent the magnitude of the evanescent wave above and at the end of the fibers;

In energy efficient tiles, roof or floor tiles; as a lighting aid in dark places, which is simply charged by room light;

In phosphor based diagnostics, such as in immunoassays which can off gate biological autofluorescence, whether blood or skin autofluorescence; and As a long wavelength tracer material which can be excited before injected into either a human or animal patient, or as a luminescent tracer through pipes or trace leakage or water flow etc.

EXAMPLES

Example 1

Near Field Effects of Metal Nanoparticles on the Photophysics of Acriflavin in PVA Polymer Matrix The photoionization of the acridine molecule in rigid glass has been known for some time, however Lim et at [25] reported the delayed fluorescence at 77K in acriflavin due to recombination of electrons with ions. Sato et at [26] proposed the origin of long lived delayed fluorescence due to the formation of an excimer in PVA sheets. Gangola et al. [27] explained the decrease in intensity and decay time with an increase in concentration as due to coulambic attraction between the charged cation and trapped electrons. However recently, fluorescence resonance energy migration phenomena has explained the decrease in decay time and red shift in delayed fluorescence with the increase in concentration of acriflavin in a PVA film [28, 29]. Efficiency of energy migration was also found maximum in acriflavin doped PVA (protic matrix) with respect to an aprotic polymer matrix [30].

Earlier, MEF studies from our group were exclusively focused on E and P type delayed emission of eosin [31] and the pyrene [32] dye respectively on glass slides with a 2.5 fold far field enhancement in fluorescence reported.

This example shows a 3.5 fold far filed enhancement is observed both in fluorescence ($S_1 \rightarrow S_0$) and delayed fluorescence ($\alpha\text{-}S_1 \rightarrow S_0$) of acriflavine doped Silver island films with respect to a control sample film (having no SiFs). These findings are helpful for understanding the photophysics of acriflavin-metal interactions and for the numerous practical applications that enhanced delayed fluorescence yield for the next generation of smart fluorescent polymers. In this regard, using MEF to increase the absolute emission intensities of luminescent plastics while simultaneously reducing the decay time, presents an opportunity for modulating (tuning) the photon flux of polymeric materials.

Materials

Acriflavin, Silane-prep glass microscope slides, Silver nitrate (99.9%), sodium hydroxide (99.996%), ammonium-hydroxide (90%), D-glucose, ethanol (HPLC/spectrophotometric grade), Polyvinyl Alcohol (PVA) [molecular weight 70,000] were purchased from Sigma-Aldrich Chemical company (Milwaukee, Wis., USA).

The synthesis of silver colloids and SiFs were prepared according to previously published procedures[6-9]. The synthesis of silver colloids was undertaken using the following procedure: 2 ml of 1.16 mM trisodium citrate solution was added drop wise to a heated (90° C.) 98 ml aqueous solution of 0.65 mM silver nitrate while stirring. The mixture was heated for 10 min, and then cooled in ice until use. This procedure yields ca. 50 nm silver colloids as confirmed by TEM analysis. Three hundred micro-liters of acriflavin dissolved in 1.0 wt % PVA in 10 ml water was spread over the SiFs coated glass slides.

Instrumentation: Absorption spectra of acriflavin on blank glass substrates and SiFs containing the PVA polymer films were collected using a single beam Varian Cary 50-Bio UV-vis spectrophotometer. Emission spectra were collected using a Varian Cary Eclipse fluorescence spectrophotometer having a pulsed xenon source for excitation. A front face sample geometry was used to undertake all the fluorescence measurements with a slit width of 5 nm, both in the excitation monochromater and emission monochromater channels. Fluorescence decays were measured using a Horiba Jobin Yvon Tem-Pro fluorescence lifetime system employing the time-correlated single photon counting (TC-SPC) technique, with a TBX picosecond detection module. The excitation source was a pulsed LED source of wavelength 372 nm having maximum repetition rate 1.0 MHz and pulse duration 1.1 nanosecond (FWHM). The intensity decays were analyzed by decay analysis software (DAS) version 6.4 in terms of the multi-exponential model:

$$I(t) = \sum_i \alpha_i \exp(-t/\tau_i) \qquad (1)$$

Where $\alpha_i$ are the amplitudes and $\tau_i$ are the decay times, $$\sum_i \alpha_i = 1.0.$$

The fractional contribution of each component to the steady state intensity is given by $$f_i = \frac{\alpha_i \tau_i}{\sum_j \alpha_j \tau_j} \qquad (2)$$

The mean lifetime of the excited state is given by $$\bar{\tau} = \sum_i f_i \tau_i \qquad (3)$$

and the amplitude-weighted lifetime is given by $$\langle \tau \rangle = \sum_j \alpha_i \tau_i \quad (4)$$

The values of $\alpha_i$ and $\tau_i$ were determined by nonlinear least squares impulse reconvolution analysis with the goodness of fit judged by the residual, autocorrelation function and $\chi^2$ values. The measurement error in decay time analysis was of the order of 0.01 ns. Photo-stability experiments where undertaken using a 405 nm laser coupled with a neutral density filter and Ocean optics spectrophotometer HP2000. Real-color photographs of the fluorescence emission were taken through an emission filter with a Canon Power shot S50 Digital Camera.

Figure 2:
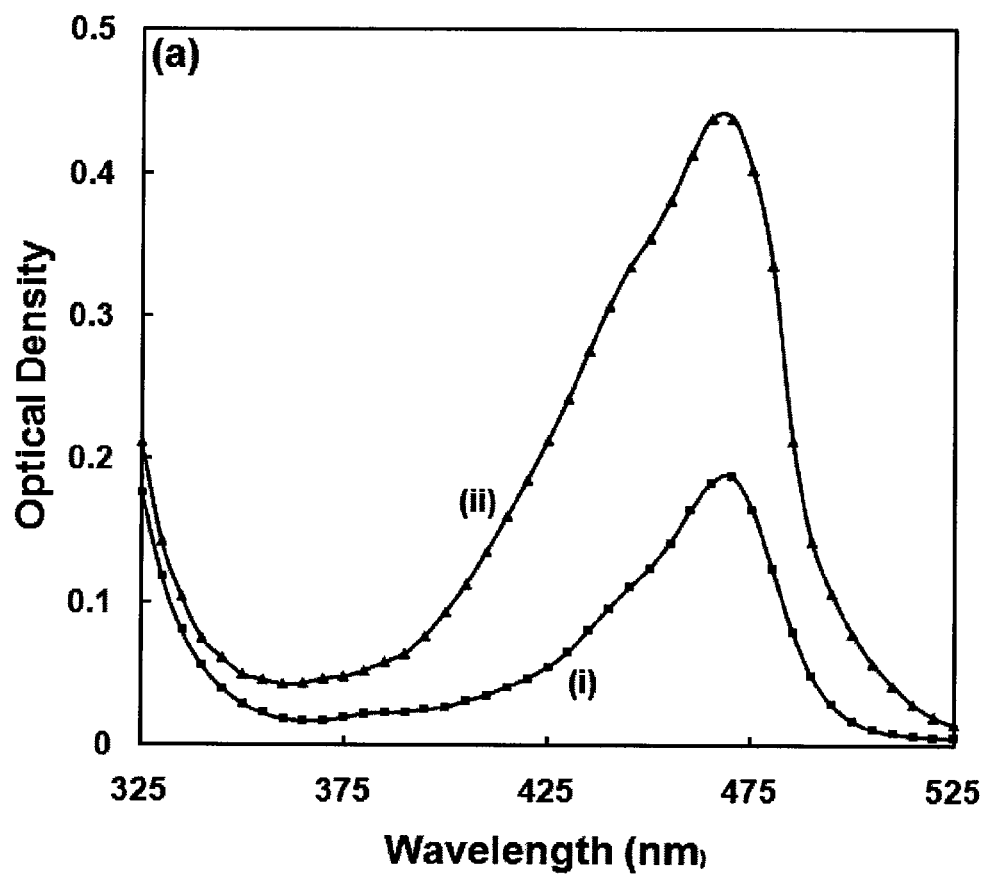
FIG. 2 shows the absorption spectra (i) PVA and (ii) Silver island films (SiFs) deposited on PVA firm ($\lambda_{ex}$=550 nm)

Results:

The absorption spectra of acriflavin doped in PVA was controlled with and without SiFs as shown in FIG. 2. The absorption maximum of acriflavin at 466 nm in PVA with an optical density≈0.18, but in the presence of SiFs, the optical density increases nearly 2 fold. This effect can be explained as a result of the coupling of the fluorophore/lumophore dipole with the localized electromagnetic field of the metallic particles, efficiently increasing the absorption cross-section of the lumophore. It is well-known that conducting metallic particles can modify the free space absorption condition in ways that increase the incident electric field, felt by fluorophores, effectively increasing the excitation rate of the fluorophore [2]. The enhanced absorption of dye molecules near metallic surfaces was firstly reported by Glass et al., [33] in 1980 and also confirmed by other groups [2-5, 34]. The absorption spectra of Acriflavin do not show any concentration dependence, which rules out the possibility of the dimer or higher aggregate formation in the ground state in this particular polymer.

Figure 3:
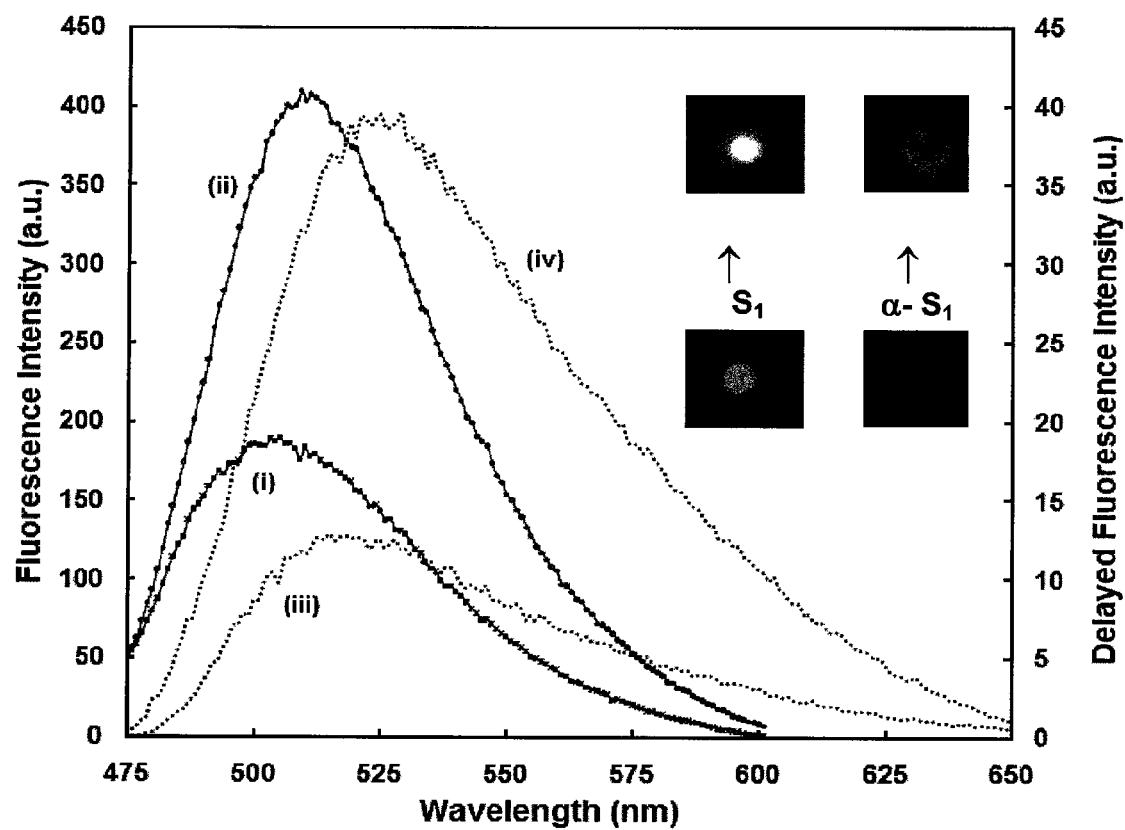
FIG. 3 shows the fluorescence spectra of acriflavin in (i) PVA and (ii) SiFs doped PVA and the delayed fluorescence spectra of acriflavin in (iii) PVA and (iv) SiFs doped PVA respectively ($\lambda_{ex}$=450 nm) Enhancement factor ~3.5. (Excitation source is a pulse xenon lamp).
Figure 4:
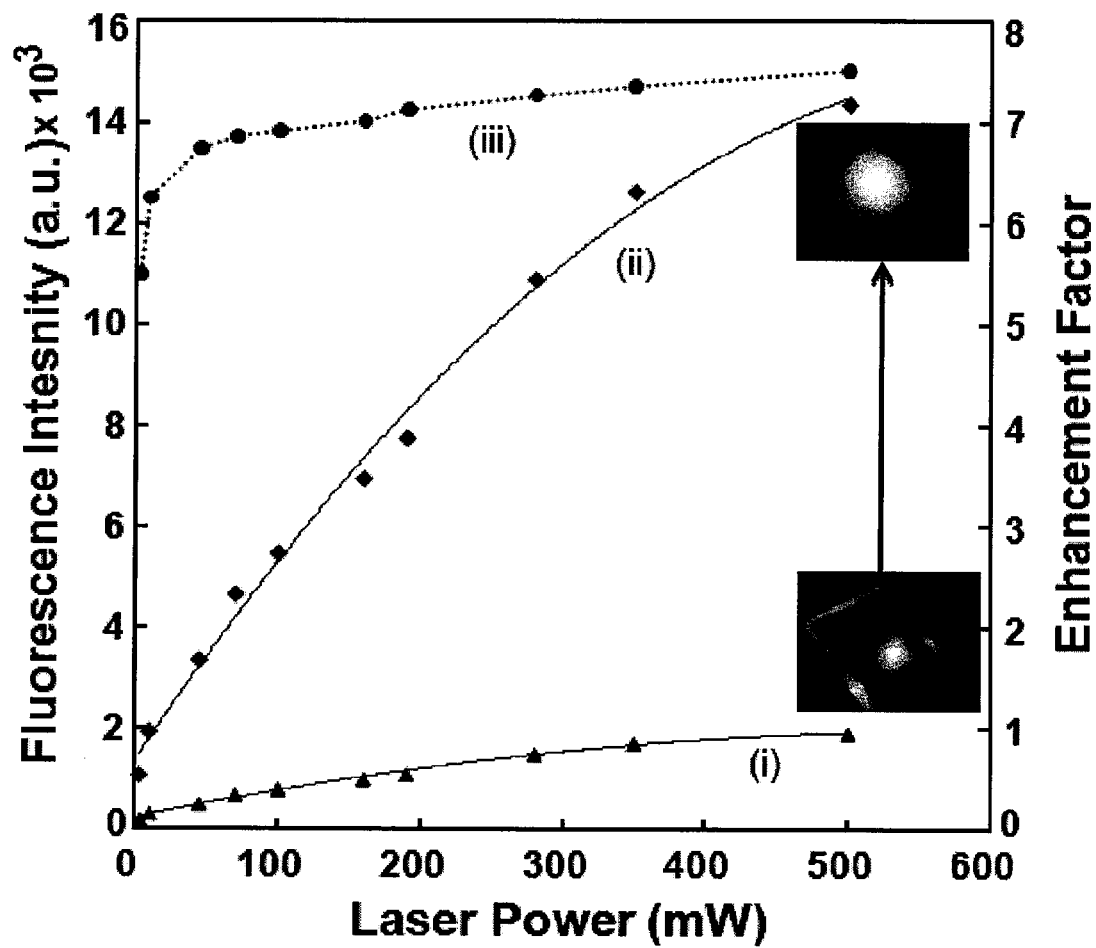
FIG. 4 shows the power dependence curve of acriflavin in (i) PVA and (ii) SiFs doped PVA ($\lambda_{ex}$=473 nm Laser), (iii) Dependence of enhancement factor with laser power.

The fluorescence and delayed fluorescence spectra of Acriflavin in PVA with and without SiFs are shown in FIG. 3. Acriflavin shows fluorescence maximum at 515 nm and a delayed emission at a 525 nm in PVA. The delayed fluorescence is nearly 10 nm red shifted as compared to fluorescence band and this shift is concentration dependent. Nearly 3.5 fold enhancement is observed both in the fluorescence and the delayed fluorescence emission from acriflavin in SiFs doped PVA films. The enhancement factor is defined as the ratio of intensity observed from SiFs (near field) divided by that from a non-silvered PVA control polymer film under otherwise identical conditions. The real color photographs in FIG. 3 show the enhanced luminescence visually. Interestingly, an excitation power dependence was observed in fluorescence enhancement with SiFs as shown in FIG. 4. The MEF factor increases exponentially≈7 times, which explains an excitation power dependence in MEF being due to the near field volume excited around the nanoparticles. The shift in the delayed fluorescence spectra with respect to $S_1$ fluorescence, suggests that the origin of this shift in emission band is due to excited state excimer formation, by the recombination of alcidine ions with trapped electrons [27].

Figure 5:
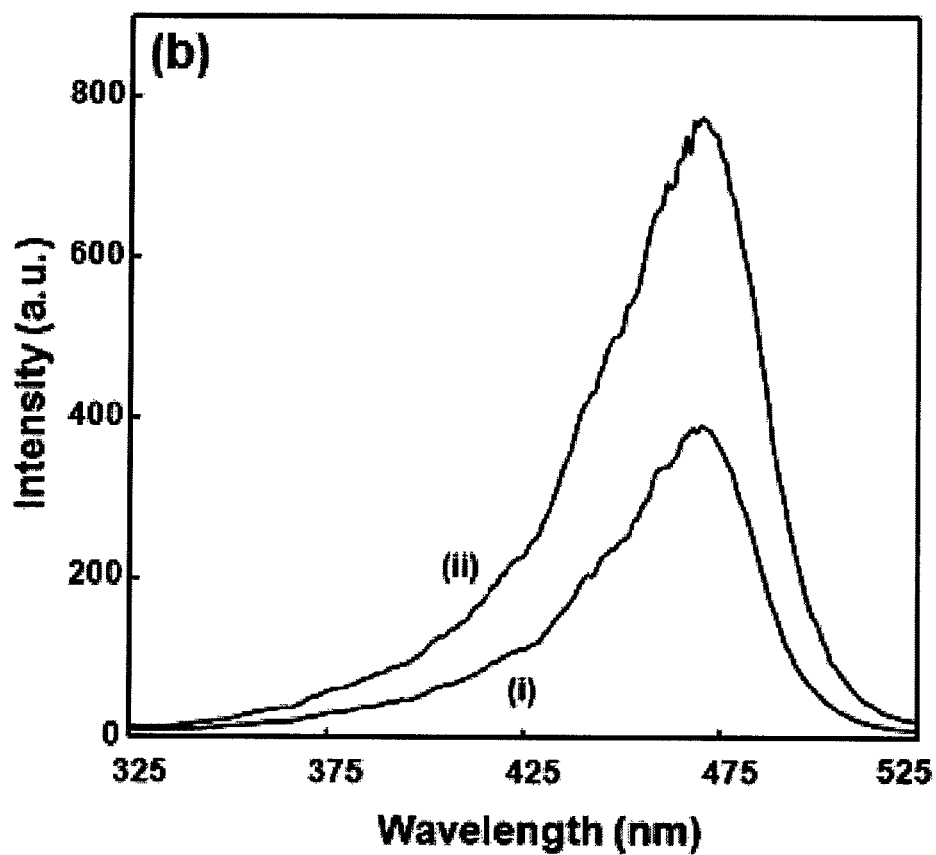
FIG. 5 shows the excitation spectra of acriflavin in (i) PVA and (ii) SiFs deposited on PVA film ($\lambda_{ex}$=550 nm).

Further to confirm the origin of the delayed fluorescence, excitation spectra were measured by monitoring the emission at blue and red edges of the fluorescence band where we see no change in the excitation spectra subsequently ruling out the potential formation of any ground state complex. Further the excitation spectra of Acriflavin were determined in PVA alone and SiFs coated PVA films, as shown in FIG. 5. In SiFs containing Acriflavin polymer films, the intensity of the excitation band increases nearly twice with respect to the PVA film alone. This resembles the absorption spectra as shown in FIG. 2.

To understand the excited state dynamics of fluorescence and delayed fluorescence of acriflavin close to metallic surface, time resolved measurements were additionally carried out using time correlated single photon counting measurements in the nanosecond ($S_1 \rightarrow S_0$) and second time ($\alpha$-$S_1 \rightarrow S_0$) range. The analyzed decay data are given in table 1 and 2 respectively, as set forth below.

TABLE 1

Time Resolved Decay parameters of Acriflavin S1 fluorescence.

| Sample | $\tau 1$ (ns) | $\alpha 1\%$ | $\tau 2$ (ns) | $\alpha 2\%$ | $\tau 3$ (ns) | $\alpha 3\%$ | $\langle \tau \rangle$ (ns) | $\tau^-$ (ns) | $\chi^2$ |
|---|---|---|---|---|---|---|---|---|---|
| PVA | 2.25 | 4 | 5.45 | 88 | 14.92 | 8 | 6.10 | 7.26 | 1.074 |
| PVA + Ag | 2.0 | 10 | 4.68 | 82 | 14.72 | 8 | 5.21 | 6.84 | 1.027 |

TABLE 2

Time Resolved Decay parameters of Acriflavin $\alpha$-S1 fluorescence.

| Sample | $\tau 1$ (s) | $\alpha 1\%$ | $\tau 2$ (s) | $\alpha 2\%$ | $\langle \tau \rangle$ (sec) | $\tau^-$ (sec) | $\chi^2$ |
|---|---|---|---|---|---|---|---|
| PVA | 0.46 | 65 | 0.80 | 34 | 0.72 | 0.62 | 1.066 |
| PVA + Ag | 0.36 | 47 | 0.68 | 53 | 0.52 | 0.58 | 1.098 |

Figure 6:
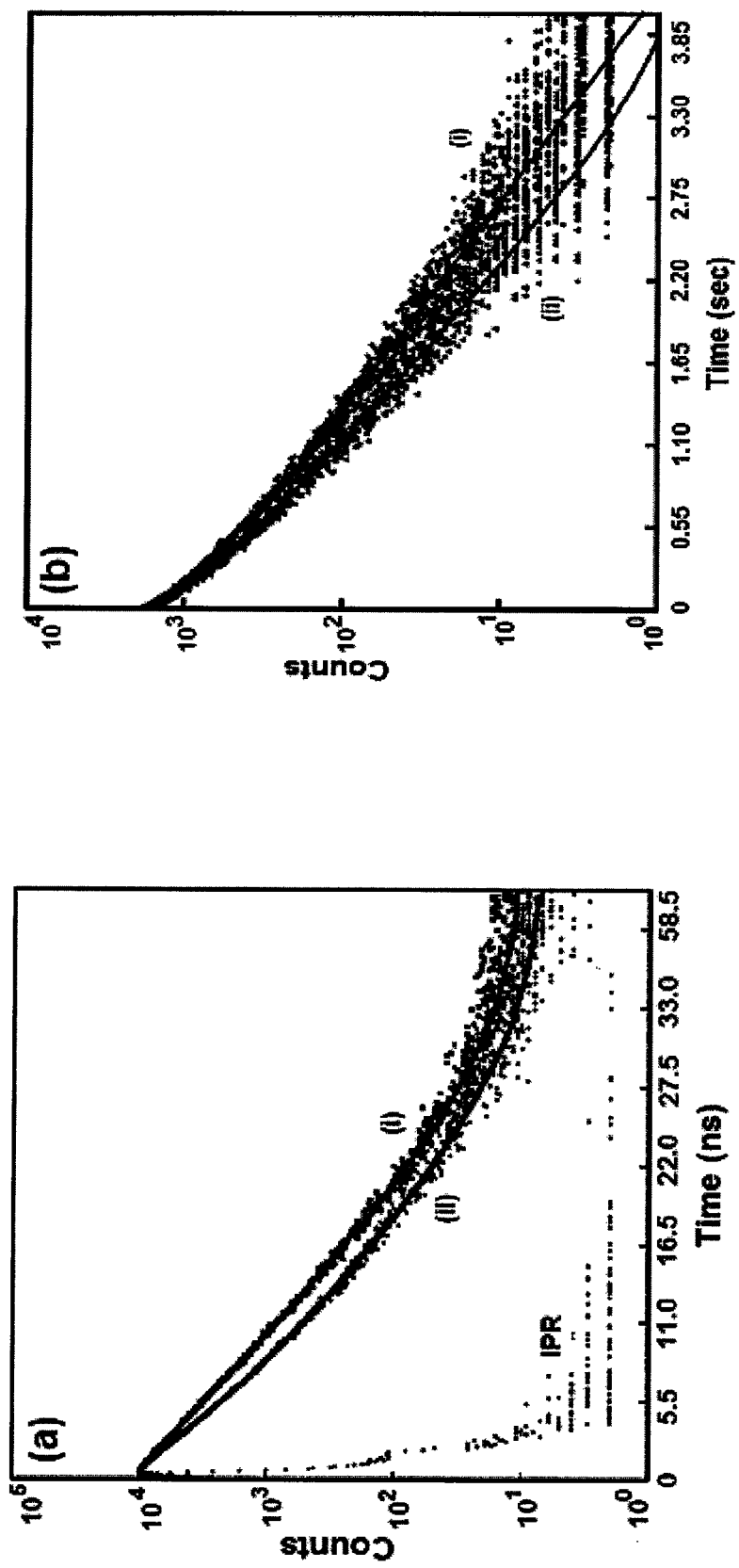
FIG. 6 shows the decay curves of (a) fluorescence and (b) delayed fluorescence of acriflavin in (i) PVA and (ii) SiFs doped PVA polymer film ($\lambda_{ex}$=455 nm).

The respective analyzed overlapped time resolved decay curves are shown in FIGS. 6(a) and (b). The fitting of the collected decay was judged by the distribution of residuals and chi-square values. It is observed that acriflavin decays triple-exponentially, with an average decay time of 7.26 ns and amplitude weighted decay time 6.10 ns in PVA and these values are found to decreases to 6.84 ns and 5.21 ns respectively in the presence of SiFs. The delayed fluorescence was found to decay bi-exponentially having an average decay time 0.62 sec, and amplitude weighted value≈0.72 sec. These values are found to be reduced to 0.58 sec and 0.52 sec respectively, in SiFs deposited PVA films. These reductions in decay times in the presence of SiFs indicate the coupling of excited states of acriflavin with plasmons of the SiFs and the subsequent nonradiative energy transfer from Acriflavin to metal particles, consistent with the MEF model postulated by Geddes [1].

Figure 7:
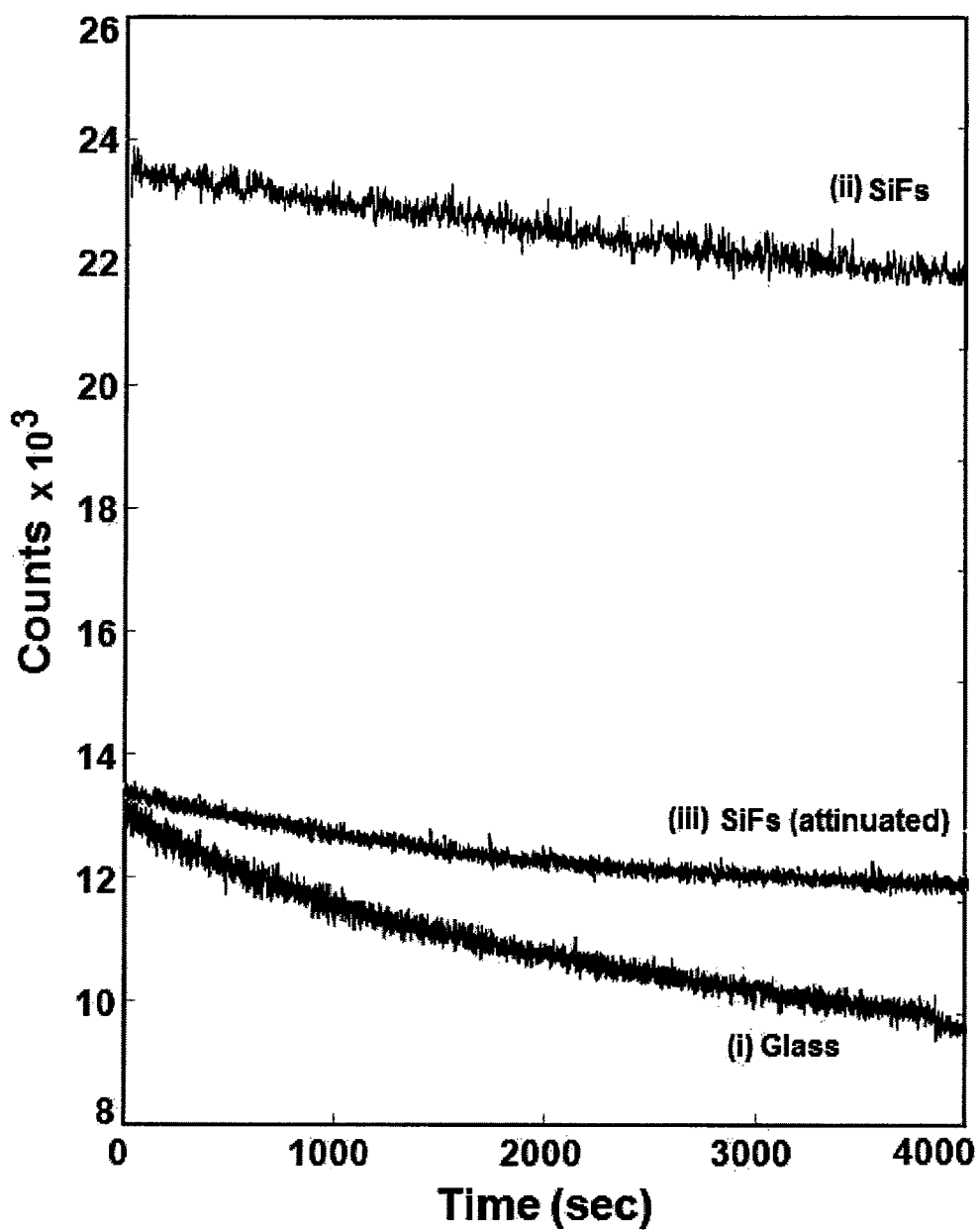
FIG. 7 shows the intensity vs. time (photostability) of acriflavin in PVA polymer film on a (i) glass slide and on (ii) SiFs. To demonstrate the benefit of SiFs, with regards to enhanced photostability, the laser power in one decay test was attenuated (iii) to given the same initial steady-state intensity as was observed on glass. ($\lambda_{ex}$=473 nm).
Figure 8:
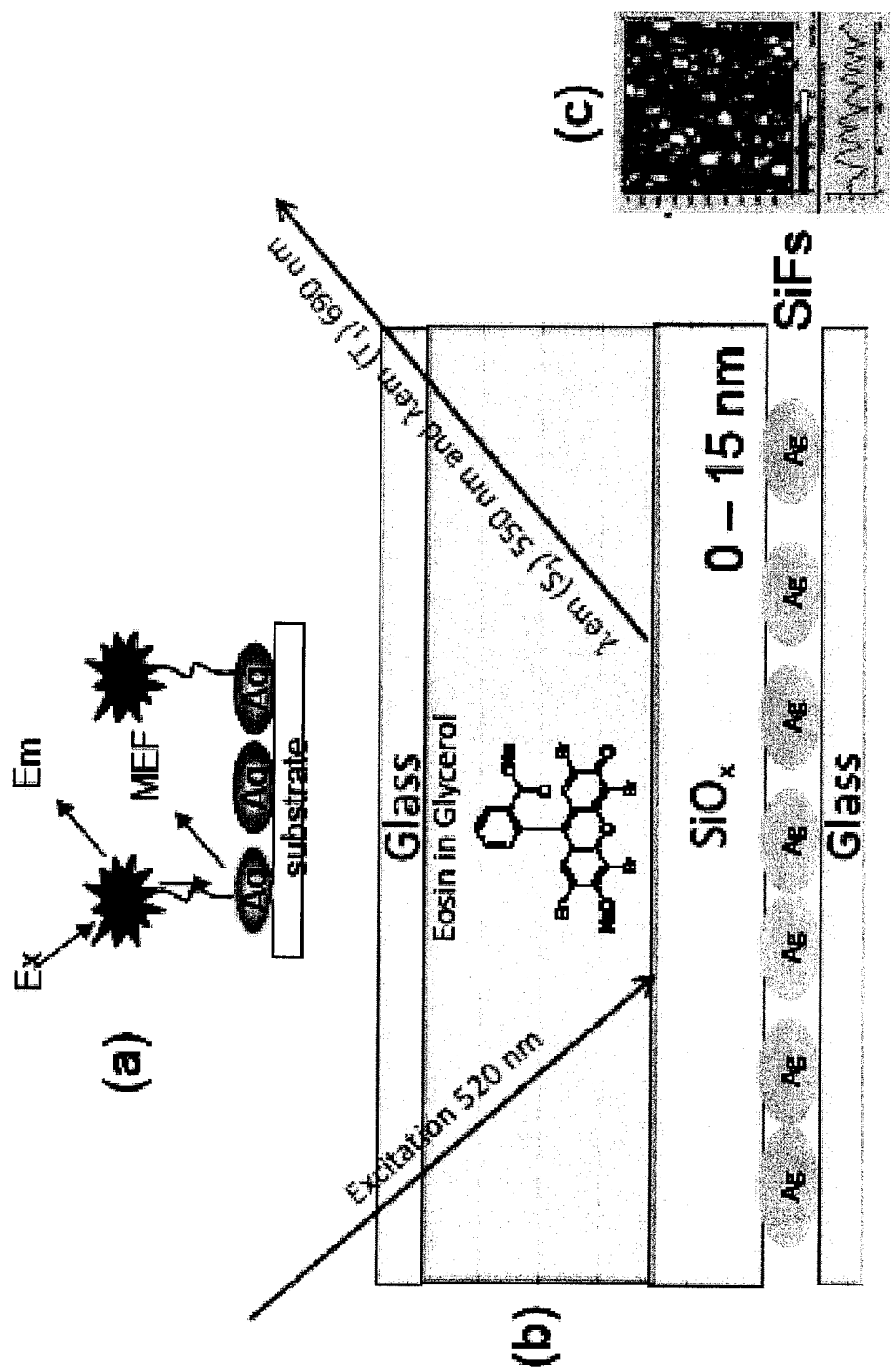
FIG. 8 (a) shows the current interpretation of Metal-Enhanced Fluorescence, (b) shows the sample geometry used to study the distance dependence of MEF for $S_1$ and $\alpha$-$S_1$ emission from eosin in glycerol on $SiO_2$ coated SiFs (silver Island Films), (c) shows AFM images of a SiFs film deposited on a glass slide.

In order to further understand metal-enhanced acriflavin fluorescence dynamics, the photostability of acriflavin in PVA films was measured with and without SiFs. These samples were exposed to a 473 nm laser line for about 300 seconds and the steady state fluorescence measured as a function of time, as shown in FIG. 7. The photostability of the acriflavin is more pronounced on SiFs containing PVA films as compared to the PVA control i.e. more photons are observed per unit time (photon flux). This finding is consistent with the reduced decay time of acriflavin near-to SiFs, Table 1, i.e. a reduced decay time and enhanced fluorescence photostability.

Two distinct observations can therefore be made for fluorescent compounds in close proximity to plasmonic nanoparticles: (1) an increase in the fluorescence emission from the metal-fluorophore unified system with the spectral properties of the fluorophores maintained, and (2) a reduction in the fluorescence lifetime, giving rise to improvements in the photostability of the fluorophores. For acriflavin, it is theorized that there are two populations of adsorbed molecules on the SiFs containing PVA films: one population is composed of more isolated molecules far from the SiFs, the photophysical properties of these similar to acriflavin in the far-field or free space condition. In the near field i.e. near to silver, an enhanced absorption and coupling to plasmons facilitates metal enhanced acriflavin fluorescence and delayed fluorescence as well as an enhanced photostability. The photo-physical properties of both fluorescence and delayed (long lived) fluorescence are found to be both drastically and favorably changed near to the metallic nano particle surfaces in such a way that an opportunity for the development of shorter lived brighter luminescent materials with a higher photon flux can be realized. One particular application of this silver doped MEF plastics lies in energy efficient plastics for lighting and safety applications, where the decay time (length of luminescent glow) and absolute brightness can be potentially tuned. An enhanced absorption and photostability is observed along with a large enhancement in both the fluorescence and delayed fluorescence as compared to an identical control sample containing no silver.

Example 2—Distance Dependence of Singlet & Triplet Character of Eosin from the Silver Nano Structured Material (SiFs)

Eosin is a red xanthene dye resulting from the reaction of bromine on Fluorescein. Due to the heavy atom effect, it shows delayed fluorescence ($\alpha$-$S_1 \rightarrow S_0$) and phosphorescence ($T_1 \rightarrow S_0$) at room temperature, along with traditional fluorescence ($S_1 \rightarrow S_0$) in the wavelength range 475 to 800 nm [62,63]. The population of the excited singlet state ($S_1$) by thermal activation of the triplet state ($T_1$) is responsible for E-type delayed fluorescence. Due to its long decay time, delayed fluorescence has been widely used to investigate the rotational diffusion time of biological macromolecules in membranes and also to characterize metal oxide surfaces [40]. Eosin is used to stain cytoplasms, collagen and muscle fibers for microscopic examination. Further it is also used for dyeing textiles, ink manufacturing, for coloring cosmetics, for coloring gasoline and as a toner, to name but just a few applications. Due to the potential uses of eosin in biology[64] and industrial research[65], distance dependent MEF studies of eosin are helpful to develop future intense fluorescent probes for studying systems in different temporal ranges i.e. from nano to millisecond time range. Zhang et. al. [66] have reported about a 2 fold enhancement in singlet-triplet emission of eosin in 4% wt. polyvinyl alcohol films coated on SiFs surfaces in recent temperature dependent studies. However, as shown below, a ~9 fold enhancement was obtained in fluorescence ($S_1 \rightarrow S_0$) and nearly a 4 fold enhancement in delayed fluorescence ($\alpha$-$S_1 \rightarrow S_0$) and phosphorescence ($T_1 \rightarrow S_0$) of eosin in anhydrous glycerol near-to SiFs with respect to a control sample containing no silver, with nearly a 20-fold enhancement of fluorescence and a 7 fold enhancement in absorption spectra both triplet and delayed emission observed near-to silver nanoparticle coated films.

Materials. Eosin, silane-prep glass microscope slides, silver nitrate (99.9%), sodium hydroxide (99.996%), ammoniumhydroxide (90%), D-glucose, ethanol (HPLC/spectrophotometric grade), anhydrous glycerol were purchased from Sigma-Aldrich Chemical company (Milwaukee, Wis., USA). The synthesis of SiFs was prepared according to previously published procedures [9-11, 39]. Twenty microliters of eosin in glycerol [$10^{-3}$M] was sandwiched between both glass and the SiFs coated silane prep slides, respectively. Different thin layers of SiOx on SiFs were prepared using an Auto 306 Vacuum coater (Accu Coat Inc., Rochester, N.Y., USA). The thickness of the deposited film was monitored using a quartz crystal microbalance.

Instrumentation: Absorption of acriflavin on blank glass substrates and SiFs containing PVA polymer films were collected using a single beam Varian Cary 50-Bio UV-vis spectrophotometer. Emission spectra were collected using a Varian Cary Eclipse fluorescence spectrophotometer having a pulsed xenon arc source for excitation. A front face sample geometry was used to undertake all the fluorescence measurements with a slit width of 5 nm, both in the excitation monochromater and emission monochromater channels. Fluorescence decays were measured using a Horiba Jobin Yvon Fluoromax-4S and Temp-Pro fluorescence lifetime system employing the time-correlated single photon counting (TCSPC) technique, with a R928 and TBX-04 picosecond detection module. The excitation source was a pulsed LED source of wavelength 372 nm having maximum repetition rate 1.0 MHz and pulse duration 1.1 nanosecond (FWHM). The intensity decays were analyzed by decay analysis software (DAS) version 6.4 in terms of the multi-exponential model:

$$I(t) = \sum_i \alpha_i \exp(-t/\tau_i),$$

where $\alpha_i$ are the amplitudes and $\tau_i$ are the decay times, $$\sum_i \alpha_i = 1.0.$$

The values of $\alpha_i$ and $\tau_i$ were determined by nonlinear least squares impulse reconvolution analysis with the goodness of fit judged by the residual, autocorrelation function and $\chi^2$ values. The measurement error in decay time analysis was of the order of 0.01 ns.

Results

Figure 9:
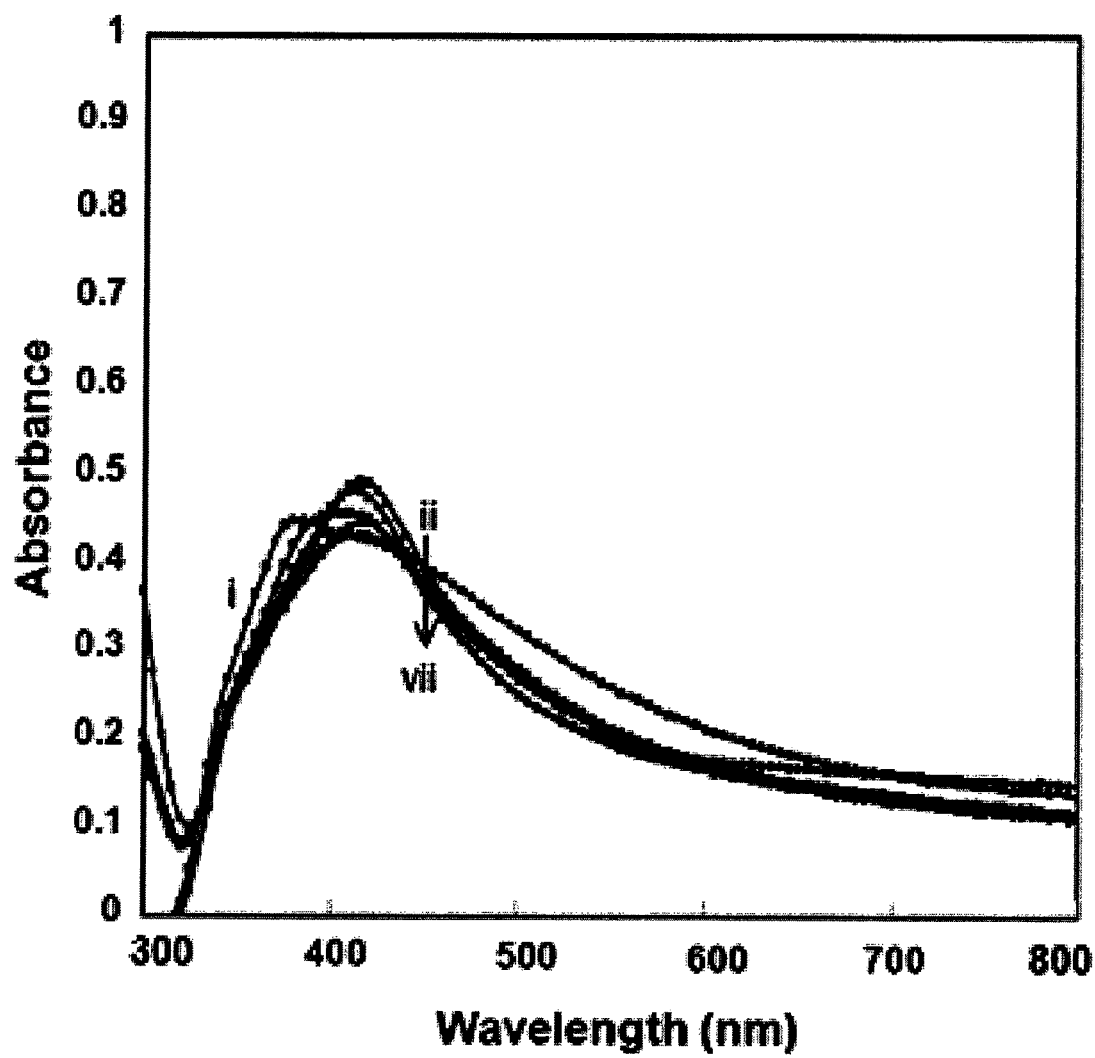
FIG. 9 shows the absorption spectra of SiFs coated with different thicknesses of $SiO_2$ (i) SiFs, (ii) 1 nm, (iii) 3 nm, (iv) 6 nm, (v) 9 nm, (vi) 12 nm and (vii) 15 nm $SiO_2$ coated on SiFs.

Silver island films (SiFs) are films comprising sub-wavelength size silver nanoparticles formed by reduction of silver nitrate on a glass surface by a wet deposition method thereby forming a film [1-3]. FIG. 9 shows the absorption spectra of SiFs and SiFs coated with different thicknesses of SiO$_X$. SiF's typically shows a structured absorption, a maxima at 390 nm along with a band at 420 nm as shown in FIG. 9(i). When quartz [SiOx] layers are coated onto SiFs deposited slides, the structured absorption of SiFs disappears, and a new red shifted band is readily observed at 400 nm. Further, on increasing the thickness of the SiOx layer, the optical density of the 400 nm band decreases as shown in FIG. 9(ii to iv). The absorption spectra of SiFs are the combinations of both absorption and scattering spectra and in the plasmonic literature, often collectively referred to as the extinction spectra. In these nanoparticle films, the absorption component is generally blue shifted and weak, while the scattering component is strong and red shifted.

Figure 10:
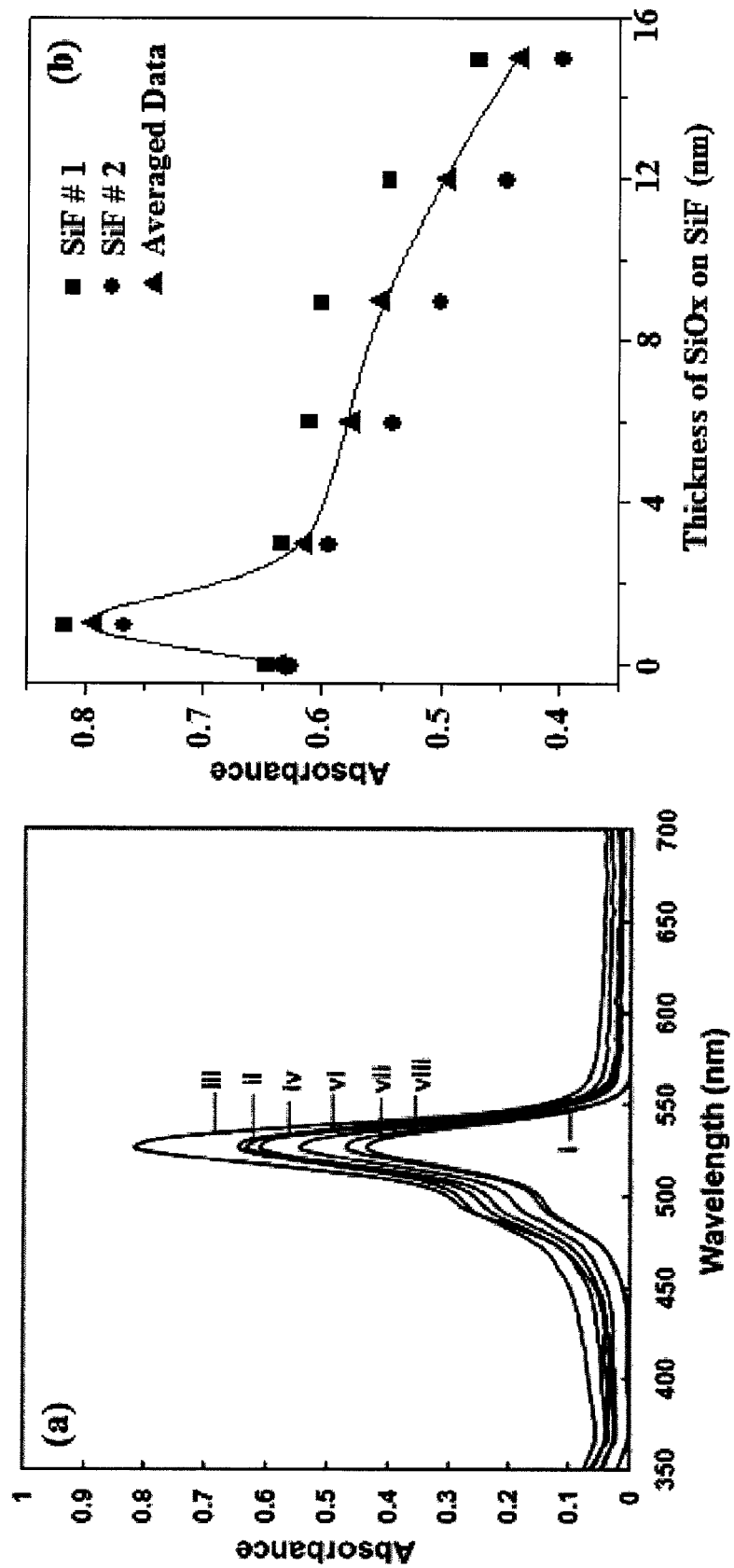
FIG. 10 (a) shows the absorption spectra of Eosin ($10^{-4}$ M) in glycerol on different thicknesses of $SiO_2$ coated Sifs. (i) Glass, (ii) SiFs, (iii) 1 nm, (iv) 3 nm, (v) 6 nm, (vi) 9 nm, (vii) 12 nm and (viii) 15 nm $SiO_2$ coated on Sifs. (b) shows the Optical Density of eosin on SiFs coated with different thicknesses of $SiO_2$.

The absorption spectra of eosin in glycerol [$10^{-4}$ M] located between two glass slides is shown in FIG. 10(a)(i). It shows an absorption maximum at 525 nm with an optical density maximum≈0.45. On SiF's, the optical density of the same increases up to 0.65 and it further increases for a 1 nm SiOx coated film (~0.82). On further increasing the thickness of the $SiO_x$ layer, the optical density decreases. The variation of enhancement in optical density of eosin on different optical density SiFs (0.45 to 0.50) coated with different thicknesses of $SiO_x$ is shown in FIG. 10(b), where the average of the absorbance of eosin was found maximum for 1 nm $SiO_x$ coated SiFs. These results indicate that when a fluorophore is placed close-to metal nanostructures, the often strong localized electromagnetic field around the metallic particles subsequently increases and the rate of absorption subsequently increases. In essence, conducting metallic particles can modify the free-space absorption condition in ways that increase the incident electric field felt by a fluorophore, i.e. an enhanced absorption cross-section.

Figure 11:
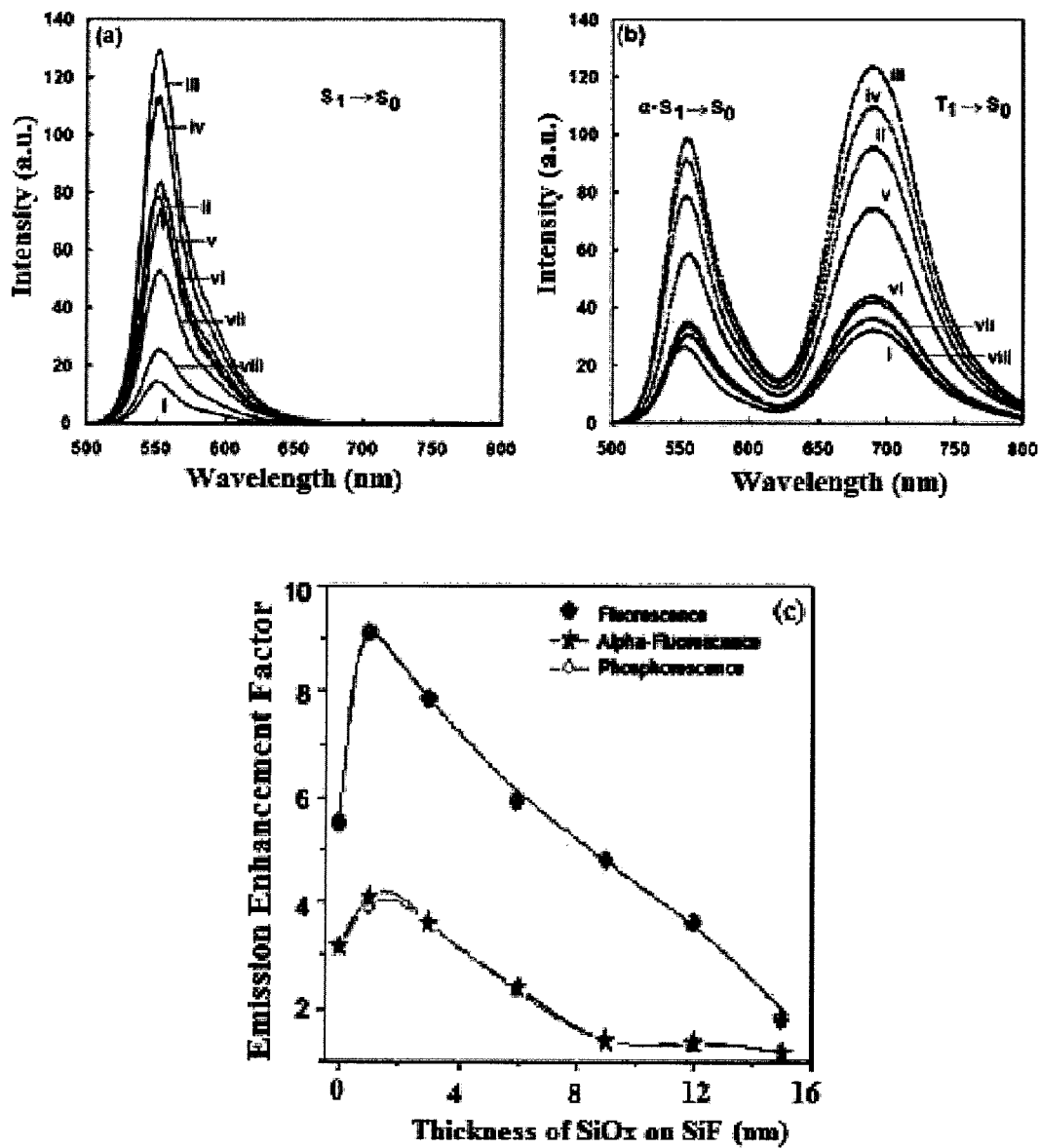
FIG. 11 (a) Fluorescence $S_1 \rightarrow S_0$ (b) delayed fluorescence $\alpha$-$S_1 \rightarrow S_0$ and phosphorescence $T_1 \rightarrow S_0$ spectra of Eosin ($10^{-4}$M) in glycerol on different thicknesses of $SiO_2$ coated SiFs. (i) Glass, (ii) SiFs, (iii) 1 nm, (iv) 3 nm, (v) 6 nm, (vi) 9 nm, (vii) 12 nm and (viii) 15 nm $SiO_2$ coated on SiFs, (c) Enhancement factor (E.F.) of eosin (i) fluorescence, (ii) alpha fluorescence and (iii) phosphorescence from SiFs coated with different thickness of $SiO_2$. E.F.—Defined as the emission from the silvered substrate divided by that from an unsilvered otherwise identical control sample.

FIGS. 11(a) and (b) show the corresponding emission spectra of eosin from singlet and triplet states respectively. Eosin shows fluorescence $[S_1 \rightarrow S_0]$ and delayed fluorescence $[\alpha\text{-}S_1 \rightarrow S_0]$ maximum at ~550 nm and phosphorescence $[T_1 \rightarrow S_0]$ maximum at ~690 nm respectively. It can be seen that eosin fluorescence enhances about 5.5 times (as compared to the control sample), while delayed fluorescence and phosphorescence enhances about 3.0 times on SiF's. Further it is interesting that the intensity of both the singlet and triplet emission again increases in the presence of a 1 nm $SiO_x$ layer, but on further increasing the thickness of the protecting $SiO_x$ layer, the enhancement of the singlet and triplet emission decreases, following the trend in optical density with thickness of $SiO_x$ as shown in FIG. 10(b). The enhancement factors for all the three emissions are shown in FIG. 11(c), where enhancement factors are defined as the emission from the silvered substrate divided by that from an unsilvered otherwise identical control sample. These results indicate that the enhanced near-field absorption has a significant bearing on enhanced luminescence photophysics.

Figure 12:
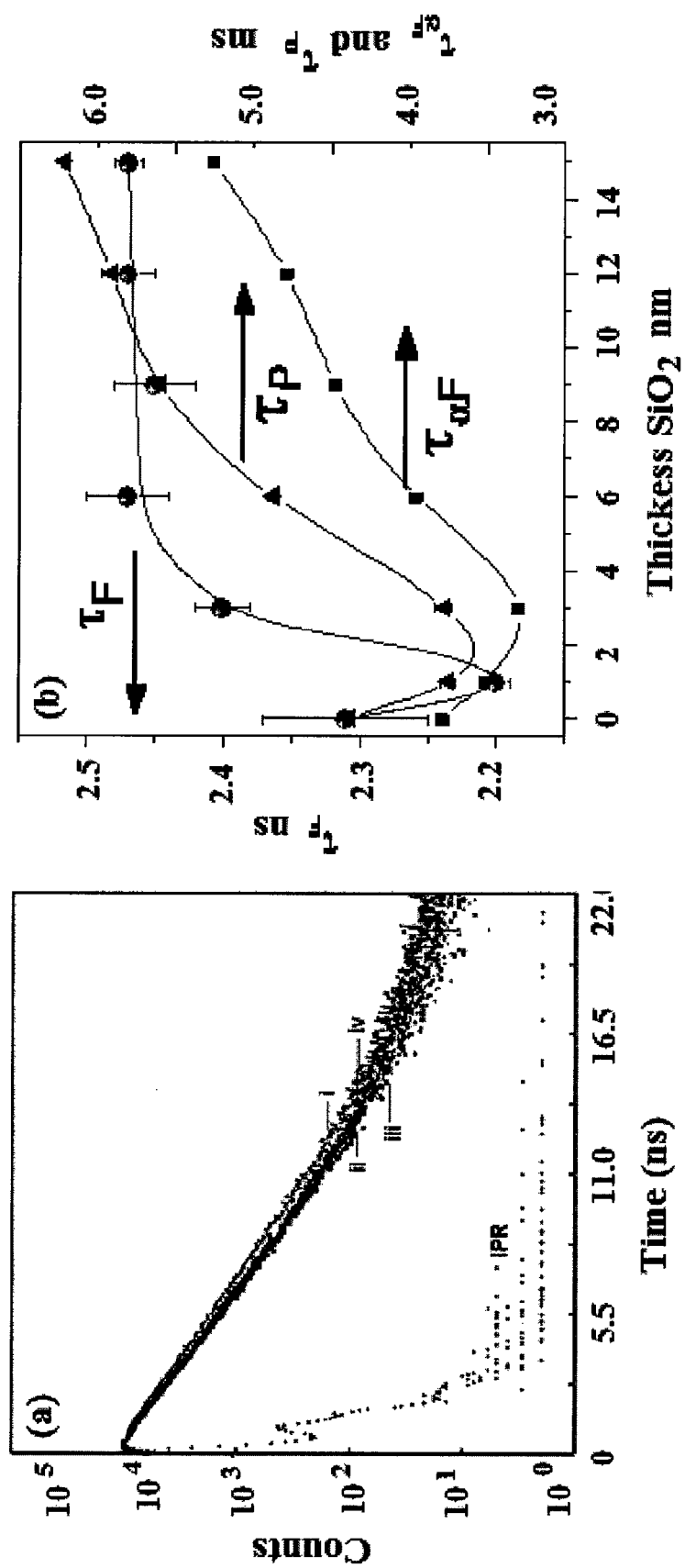
FIG. 12 (a) shows the decay curves of the fluorescence of eosin ($10^{-4}$ M) in glycerol (i) on a glass slide, (ii) on SiFs, (iii) 1 nm $SiO_2$ coated on SiFs and (iv) 3 to 15 nm $SiO_2$ coated on SiFs, (b) Variation of decay time components of eosin (i) fluorescence, (ii) alpha fluorescence and (iii) phosphorescence from SiFs coated with different thicknesses of $SiO_2$.

To further understand the fluorescence dynamics of the singlet and triplet states of eosin near-to the SiF's, decay time measurements were undertaken with different layers of $SiO_x$, the time resolved results tabulated in Table 3, as shown below.

thickness of the protecting layer is shown in FIG. 12(b). It can be seen that the magnitude of the decay values shows a decrease with the 1 nm layer of SiOx, and then further increases with an increased distance from the SiFs. Further, a decrease was observed in the delayed fluorescence decay time $\tau_{\alpha F}$ on SiFs~3.28 ms for the eosin dye molecule near-to silver as compared to glass~4.71 ms and a decrease in phosphorescence decay time $\tau_P$ on SiFs~3.88 ms near-to silver is observed as compared to glass~6.80 ms. The magnitude of both the decay values shows a decrease with the 1 to 3 nm layer of SiOx, and then further increases with an increased distance from the SiFs similar to the fluorescence decay as shown in FIG. 12(b). The metal enhanced phosphorescence decay time is shorter, as expected, than the metal-enhanced delayed fluorescence lifetime. These findings are consistent with fluorophores that do not exhibit delayed fluorescence MEF [8-12, 40] and MEP [41-43].

Subsequently in this work, 2D finite-difference time-domain (FDTD) simulations were also undertaken using Lumerical FDTD Solution software (Vancouver, Canada) to study the near-field relative electric field intensities and distributions around silver nanoparticles (NP), and to study how the E-field effect correlates with the observed changes in the distance dependence of metal enhanced fluorescence (MEF) for Ag—$SiO_x$ sample embodiments. The simulation region was set to 600×600 nm² with a high mesh accuracy. To minimize simulation times and maximize the resolution of field enhancement around the metal particles, a mesh override region was set to 0.1 nm. The overall simulation time was set to 100 fsec; calculations were undertaken over the wavelength range 300 to 600 nm. In these simulations the incident field is defined as a plane wave with a wave-vector that is normal to the injection surface (depicted as a white arrow in FIG. 13) and the scattered and total fields are monitored during the simulation such that the total or scattered transmission can be measured. Further, distributions of e-fields around different layers of $SiO_x$ coated silver nanoparticles and their extinction cross-section upon intensity of the incident light were also undertaken to rationale the distance dependence e-field prorogation around nanoparticles.

| Sample | τ (ns) [S1 → S0] | τ (ms) [αS1 → S0] | τ (ms) [T1 → S0] | χ2 [S1] | χ2 [αS1] | χ2 [T1] |
| --- | --- | --- | --- | --- | --- | --- |
| Glass | 2.65 ± 0.02 | 4.71 ± 0.04 | 6.80 ± 0.02 | 1.461 | 1.373 | 1.299 |
| SiFs | 2.31 ± 0.06 | 3.28 ± 0.03 | 3.88 ± 0.03 | 1.211 | 1.377 | 1.062 |
| 1 nm SiO2 | 2.20 ± 0.01 | 3.01 ± 0.03 | 3.25 ± 0.04 | 1.181 | 1.435 | 1.121 |
| 3 nm SiO2 | 2.40 ± 0.02 | 2.8 ± 0.02 | 3.28 ± 0.05 | 1.341 | 1.381 | 1.135 |
| 6 nm SiO2 | 2.47 ± 0.03 | 3.45 ± 0.04 | 4.37 ± 0.03 | 1.242 | 1.242 | 1.168 |
| 9 nm SiO2 | 2.45 ± 0.03 | 3.97 ± 0.03 | 5.09 ± 0.03 | 1.168 | 1.148 | 1.164 |
| 12 nm SiO2 | 2.47 ± 0.02 | 4.29 ± 0.04 | 5.41 ± 0.02 | 1.612 | 1.151 | 1.180 |
| 15 nm SiO2 | 2.47 ± 0.01 | 4.75 ± 0.01 | 5.71 ± 0.02 | 1.311 | 1.176 | 1.181 |

Figure 13:
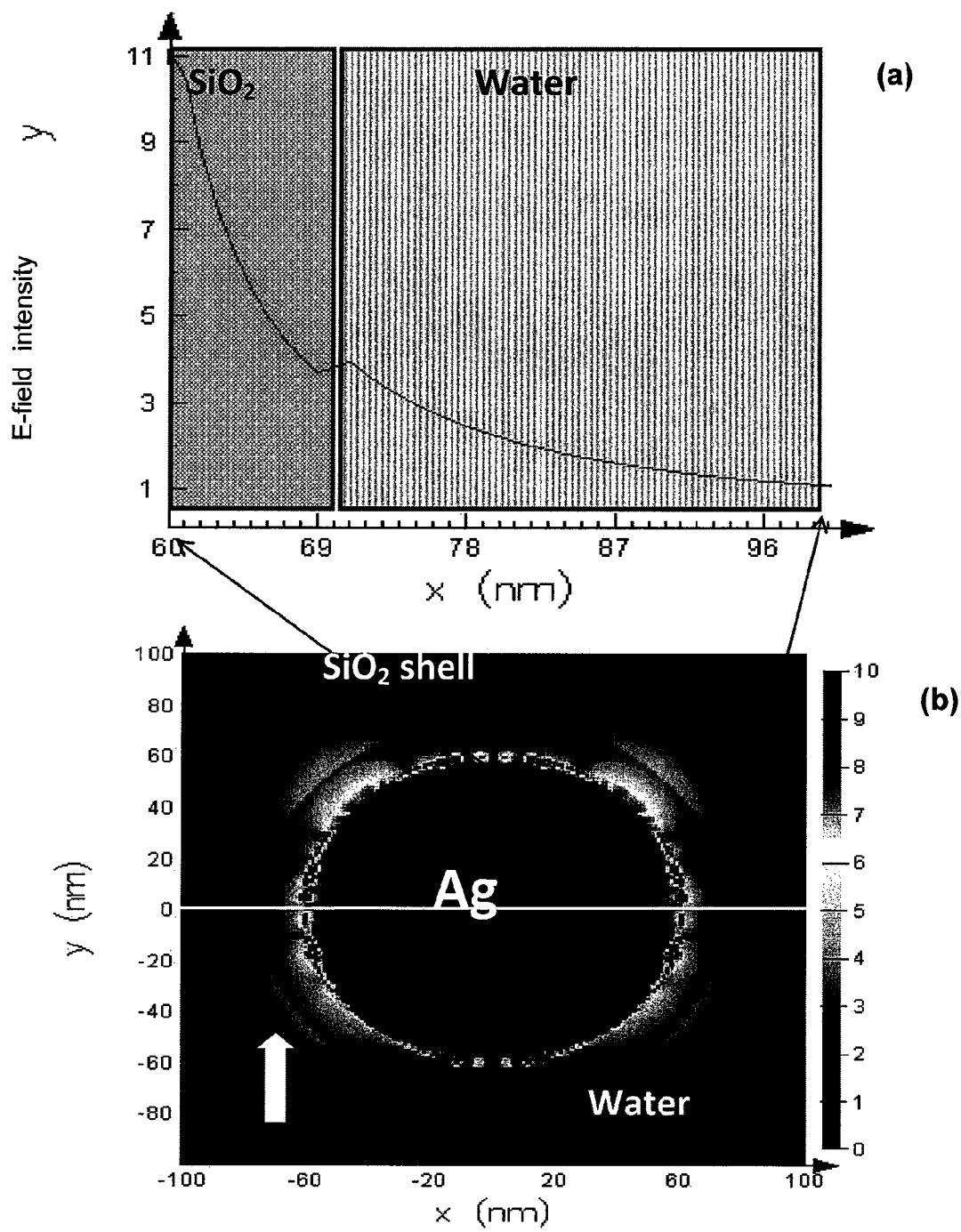
FIG. 13(a) shows the decay of the E-field intensity upon the distance from an Ag—NP. The E-field was calculated from the 2D FDTD simulation for the system: the 120 nm silver core of the nanoparticle is covered with a $SiO_2$ shell of 10 nm thickness. (b) The 2D distribution of the E-field around the NP. Arrow shows the direction of incident light at a 400 nm wavelength. Red arrows show the axis along which the E field intensity was calculated. [NP—Nanoparticles].
Figure 14:
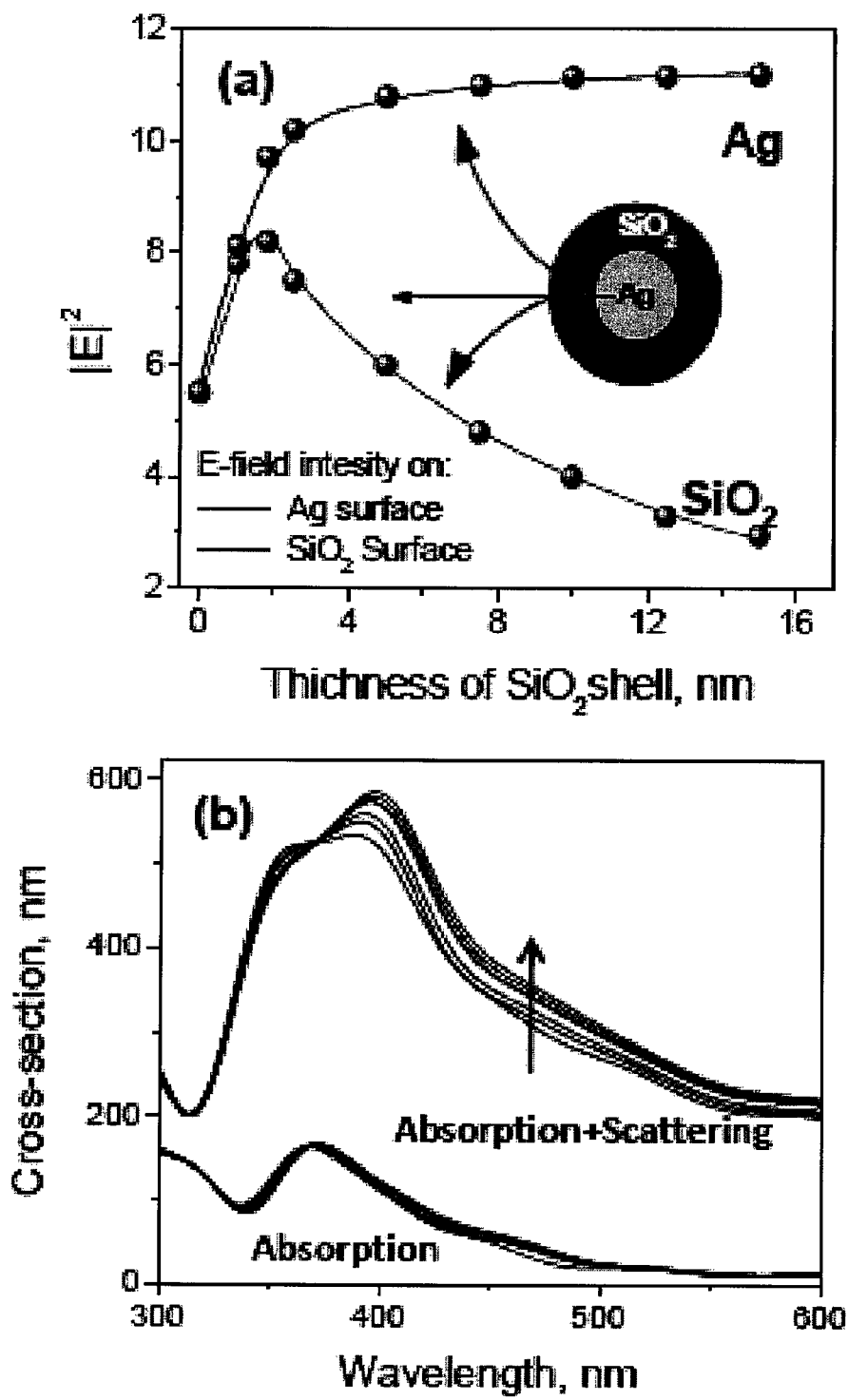
FIG. 14(a) shows that the E-field on the silver surface increases almost 2-fold upon depositing $SiO_2$ on the nanoparticle surface, i.e. upon the change of polarity of the NP environment, while on the surface of a glass shell the intensity of the E-field increases and then decays with the distance (glass thickness) from the Ag-NP surface, (b) Extinction and absorption spectra of a Ag-NP covered with glass of different thicknesses, from 0 to 15 nm. Plasmon scattering component of silver NP extinction spectra increases upon thickness of the $SiO_2$ shell.

The fluorescence of the eosin molecule decays single exponentially with a decay time of 2.65 ns in glycerol measured in between the two glass slides, which similarly has been observed previously by Flaming et. al. [62]. It is interesting to note that the fluorescence decay of eosin becomes a double exponential with decay times 2.31 ns and 0.05 ns. The amplitude of the longer decay time is 70% while the decay amplitude of shorter decay time is nearly 30%. Further decreases in magnitude of both decay components, is observed for a 1 nm layer of SiOx, while the magnitude of both the decay times increases with an increase in the thickness of the $SiO_x$ as shown in FIG. 12(a). The change in longer decay time ($\tau_F$) with the change in Decay of the E-field intensity as a function of distance from a Ag-NP is shown in FIG. 13—top. The E-field was simulated for a 120 nm silver core nanoparticle covered with an $SiO_2$ shell of 10 nm thickness. The bottom FIG. 13 shows the 2D distribution of the E-field around the NP. While the white arrow shows the direction of incident light injection, the red arrows show the axis along which the E intensity was calculated (see Top FIG. 13). FIG. 14. (Top) shows that the E-field on the silver surface increases almost 2-fold upon depositing $SiO_2$ which we attribute to the change in polarity and reflective index of the NP's environment, while on the surface of the glass shell the intensity of the E-field increases and then decays with distance. Interestingly, the plasmon scattering component of the silver NP extinction spectra (FIG. 14 bottom) increases upon thickness of the $SiO_2$ shell. These results are in very good agreement with the experimental observations as shown in FIG. 9.

Figure 15:
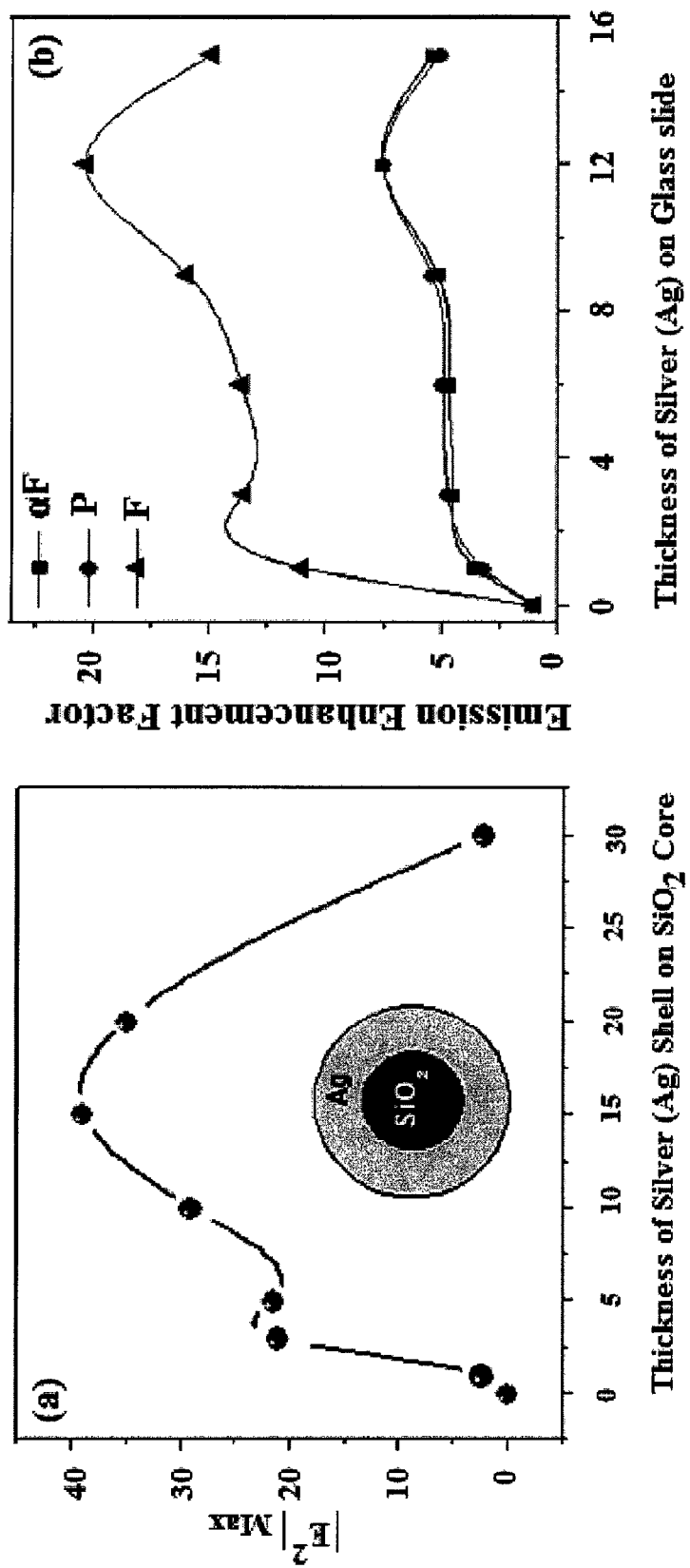
FIG. 15(a) shows the distance of the near field intensity around a NP (core Glass (SiOx) 120 nm) upon thickness of the silver shell for a wavelength of 468 nm. (b) Enhancement factor (E.F.) of Eosin (i) fluorescence, (ii) alpha fluorescence and (iii) phosphorescence experimentally determined from silver coated at different thickness on the glass slide. E.F.—Defined as the emission from the silvered substrate divided by that from an unsilvered otherwise identical control sample.

To further understand e-field enhancements, FDTD calculations were also undertaken for the inverse sample embodiment. These results indicate that maximum MEF will occur for a system having a 10 to 20 nm silver layer on 120 nm $SiO_x$ FIG. 15(a). These results are also in very good agreement with the associated experimental findings of MEF [67], but surprisingly, no initial decrease in luminescence is observed as in FIG. 14—top for the alternative samples embodiment, FIG. 15(b). This suggests that the numerous reports of decreased fluorescence of $SiO_2$ coated Ag, may be simply reflecting decreased electric field intensity, as compared to reports of close range fluorescence quenching.

Finally, it was found that a 1 nm layer of SiOx was found to yield maximum absorption, singlet & triplet emission enhancement along with a corresponding maximum decrease in luminescence decay time. Further a very good correlation was observed in these experimental findings with theoretical FDTD numerical simulations. Surprisingly, the FDTD results suggest that a decrease in emission below 1 nm is due to a change in microenvironment/refractive index of the $SiO_x$ layer and not due to quenching of the fluorophore, as reported by others. Further, on comparing these results with the distance dependence of fluorescence for different layers of metal on glass, it appears that the maximum enhancement occurs for a 15 to 20 nm silver thickness or diameter.

REFERENCES

The contents of all references set forth below are incorporated by reference herein for all purposes.
1. Metal-Enhanced Fluorescence; Ed. Geddes, C. D.; 2010, Wiley International, USA.
2. J. R. Lakowicz, K. Ray, M. Chowdhury, H. Szmacinski, Yi Fu, J. Zhang, K. Nowaczyk *Analyst,* 133, (2008) 1308.
3. Geddes, C D, J. R. Lakowicz, J. Fluor., 12, (2002) 121-129.
4. Lakowicz, J. R., *Anal. Biochem,* 337 (2005) 171.
5. Aslan, K., Z. Leonenko, J. R. Lakowicz, C. D. Geddes, J. Fluore, 15 (2005), 643.
6. www.theinstitute of fluorescenec.com\publications.
7. Aslan, K., I. Gryczynski, J. Malicka, E. Matveeva, J. R. Lakowicz, C. D. Geddes, *Current Opinion in Biotech.,* 16: (2005) 55.
8. Aslan, K., Geddes, C. D. *Chem. Soc. Rev.,* 2009, 38, 2556.
9. Aslan, K., Huang, J., Wilson, G. M., and Geddes, C. D. (2006). *J. Am. Chem. Soc.,* 128, 4206-4207.
10. Aslan, K., Holley, P., Geddes, C. D. (2006). *J. Immuno Methods,* 312, 137-147
11. Aslan, K. and Geddes, C. D. (2009) *Plasmonics,* 4(4), 267-272.
12. Zhang, Y., Aslan, K., Previte, M. J. R. and Geddes, C. D. (2008) *PNAS,* 105 (6), 1798-1802.
13. Aslan, K., Badugu, R., Lakowicz, J. R., and Geddes, C. D. (2005)., *J. Fluo,* 15(2), 99-104.
14. Aslan, K., Holley, P., Geddes, C. D. (2006)., *Journal of Materials Chemistry,* 16(27), 2846-2857.
15. Lee, K., Zhang, H., et al., *PNAS* 2009 106:17910.
16. Lee P S, Shin D H, Lee K M, Song S, Yoo H S, Moon D C, Hong J T, Chung Y B *Arch Pharm Res;* 30, 2007, 372.
17. Kawai, M., Yamagishi, J I., *Microbiol. Immuno.,* 2009, 53 (9), 481.
18. Kawai M, Yamada S, Ishidoshiro A, Oyamada Y, Ito H, Yamagishi, *J Med Microbiol;* 2009; 58 (3):331.
19. Keyhani E, Khavari-Nejad S, Keyhani J, Attar F, Ann N Y, *Acad Sci;* 1171, 2009; 284.
20. Isenberg, R. B. Leslie, S. L. Baird, Jr., R. Rosenbluth, R. Bersohn; *PNAS,* 1964, 52(2), 379.
21. Perkins, D. D., Raju, N B., et al. *Genetics* 141, 1995. 909.
22. Misra, V., Mishra, H., et al., *Sens. Actua. B,* 63 (2000) 18.
23. Misra, V., Mishra, H., et al., *Sens. Actua. B,* 82 (2002) 133.
24. Birks, J B., Photophysics of Aromatic Molecules, Wiley Interscience, 1970.
25. Lim, E C., Swenson; W., *J. Chem. Phys.* 36 (1962) 118.
26. Sato, M., T. Azumi, T., *Bull. Chem. Soc.* Japan, 40, 1967, 1031.
27. Gangola, P G., Joshi, N B., *Current Science,* 20 (1981) 711.
28. Kaputskayaa, I A., Ermilovb, E A., et al., *J. Lumin.* 121 (2006) 75.
29. Kaputskayaa, I A., Ermilovb, E A., et al., *Chem. Phys.* 327, 2006, 171.
30. Misra, V., Mishra, H., *J. Phy Chem. B;* 2008 112, 4213.
31. Zhang, Y.; Aslan, K.; Previte, M. J. R.; Geddes, C. D. *Chem. Phys. Lett.,* 458, (2008), 147.
32. Zhang, Y.; Aslan, K.; Previte, M. J. R.; Geddes, C. D. *Appl. Phys. Lett.,* 92, (2008), 013905.
33. A. M. Glass, A M., Liao, P F., et al., *Opt. Lett.* 5 (1980)368.
34. Wang, S., Boussaad, S., et al., *Rev. Sci. Instr.* 7, 2006, 3055.
35. Fister, J C., Harris, J M., *Anal. Chem.* 68, (1996),639.
36. Dragan, A I., Pribik, R., Geddes, C D., *J. Am. Chem. Soc.* 2010 (submitted).
37. Aslan K.; Malyn S. N.; Geddes C. D. J. Fluore. 2007, 17, 7-13.
38. Aslan, K., Lakowicz, J. R., Szmacinski, H., and Geddes, C. D. *J. Fluore.* 2004, 14, 6, 677-679.
39. Aslan, K.; Geddes C. D. *Anal. Chem.* 2009, 81, 6913-6922.
40. Chowdhury, M. H., Aslan, K. and Malyn, S. N., Lakowicz, J. R., Geddes, C. D. *Appl. Phys. Lett.,* 2006, 88, 173104.
41. Zhang, Y., Aslan, K., Malyn, S. N., Geddes, C. D. *Chem. Phys. Lette.,* 2006427, 432-437.
42. Zhang, Y., Aslan, K., Previte, M. J. R., Malyn, S. N., and Geddes, C. D., *J. Phys. Chem. B,* 2006, 110, 25108-25114.
43. Previte, M. J. R., Aslan, K., Zhang, Y., Geddes, C. D. *Chem. Phys. Lette.,* 2006432, 610-61.
44. Zhang, Y., Aslan, K. and Geddes, C. D. *J. Fluore.,* 2009, 19, 363-367.
45. Dragan, A. I., Zhang, Y. and Geddes, C. D. *J. Fluore.,* 2009, 19 (2), 369-374.
46. "Radiative Decay Engineering"—Topics in Fluorescence Spectroscopy Vol. 8, Ed. Geddes, C. D.; Lakowicz, J. R., Springer, New York, 2004.
47. Tarcha P. J.; Gonzalez J. D.; Llorente S. R.; Aroca R. *Appl. Spec.* 1999 53-58,
48. Tovmachenko O. G.; Graf C; Heuvel D. J. V. N.; Blaaderen A. V.; Gerritsen H. C. *Adv. Mater.* 2006, 18, 91-95.
49. Chen Y.; Munechika K.; Ginger, D. S. *Nano Lett.,* 2007, 7, 690-696.
50. Kiummerlen J.; Leitner A.; Brunner H.; Aussenegg F. R.; Wokaunt A.; *Mole. Phys.,* 1993, 80, 1031-1046.
51. Jin Y. D.; Gao X., *Natu. nanotech.* 2009, 193-197.

52. Cheng D.; Qing-Hua X. *Chem. Comm.*, 2007, 248, 248-250.
53. Malicka J.; Gryczynski I.; Gryczynski Z.; Lakowicz J. R. *Analy. Bio.* 2003, 315, 57-66.
54. Ray K.; Badugu R.; Lakowicz J. R. *Chem. Mater.* 2007, 19, 5902-5909.
55. Ray K.; Badugu R.; Lakowicz J. R. *Langmuir.* 2006, 26 8374-8378.
56. Ray K.; Badugu R.; Lakowicz J. R. *J. Phys. Chem. C* 2007, 111, 7091-7097.
57. Zhang J.; Fu Yi.; Chowdhury M. H.; Lakowicz J. R. *J. Phys. Chem. C* 2007, 111, 11784.
58. Aroca R.; *Langmuir* 1988, 4, 518-521.
59. Barnes W. L.; J. *Modern Phys.* 1998, 45, 661-699.
60. Stoermer R. L.; Keating C. D. *J. Am. Chem. Soc.,* 2006 128, 13243-13254.
61. Okhamoto, K; Niki, I.; Shvartser, A.; Narukawa, Y.; Mukai, T.; Scherer, A.; *Nature Materials,* 2004, 3, 601-605.
62. Flaming, G. R.; Knight, A. W. E.; Morris, J. M.; Morrison; Robinson, G. W. *J. Am. Chem. Soc.* 1977, 99, 4306-4311.
63. Geddes, C. D. *Meas. Sci. Technol.* 2001, 12, R53-R88
64. Llewellyn B. D. 2009, 84, 159-177.
65. Edward G., *Synthetic dyes in biology, medicine and chemistry* Academic Press, London, England 1971.
66. Zhang Y, Dragan A, Geddes C. D. *J. Phys. Chem. C.* 2009, 113, 12095-12100.
67. J. Zhang, Yi Fu, J. Lakowicz, *J. Phys. Chem. C* 2009, 113, 19404-19410.

That which is claimed is:

1. A method for increasing radiative decay and/or increased emission intensity, the method comprising:
    providing a substrate having a surface, wherein the substrate is coated with a metallic material that exhibits surface plasmons on excitation, wherein the metallic material is silver, gold, copper, and combinations thereof and wherein the metallic material is in the form of metallic islands, shaped metallic nanostructures, or metallic colloids;
    coating the metallic material with a SiOx layer, wherein the SiOx layer is about 1 nm thick;
    coupling a long lived luminescent compound selected from a delayed fluorescent compound or phosphorescent compound to the SiOx layer covering the metallic material, wherein the long lived luminescent compound coupled to the SiOx layer is positioned at a distance from the metallic material of about 1 nm that provides for coupling interaction between the long lived luminescent compounds and excited metallic surface plasmons; and
    irradiating the long lived luminescent compound in an amount sufficient to excite the long lived luminescent compound causing an interaction with the surface plasmons of the metallic material thereby increasing radiative decay and/or increased singlet and triplet emission intensity of the long lived luminescent compound.

2. The method of claim 1, wherein the shaped metallic nanostructures have a cross-section selected from triangle, square, rectangle, trapezoid, or combinations thereof and having a thickness from about 45 nm to about 250 nm.

3. The method of claim 1, wherein the substrate is a polymeric material, glass, paper, nitrocellulose, of a combination thereof.

4. The method of claim 1, wherein the long-lived luminescent compound are evenly distributed, randomly distributed or patterned on the coating encompassing the metallic core.

5. The method of claim 1, wherein the long-lived luminescent compound has a luminescence lifetime equal to or more than 1 microsecond.

6. The method of claim 1, wherein the long-lived luminescent compound is a phosphor selected from the group consisting of $Zn_2SiO_4$:Mn (Willemite); ZnS:Ag+(Zn,Cd)S:Ag; ZnS:Ag+ZnS:Cu+$Y_2O_2$S:Eu; ZnO:Zn; ZnS:Ag,Cl; ZnS:Zn; $(KF,MgF_2)$:Mn; (Zn,Cd)S:Ag; (Zn,Cd)S:Cu; $Y_2O_2$S:Eu+$Fe_2O_3$, ZnS:Cu,Al; ZnS:Ag+Co-on-$Al_2O_3$; (KF, $MgF_2$):Mn; (Zn,Cd)S:Cu,Cl; ZnS:Cu; ZnS:Cu,Ag; $MgF_2$:Mn; $(Zn,Mg)F_2$:Mn; $Zn_2SiO_4$:Mn,As; ZnS:Ag+(Zn,Cd)S:Cu; $Gd_2O_2$S:Tb; $Y_2O_2$S:Tb; $Y_3Al_5O_{12}$:Ce; $Y_2SiO_5$:Ce; $Y_3Al_5O_{12}$:Tb; ZnS:Ag,Al; ZnS:Ag; ZnS:Cu,Al; ZnS:Cu, Au,Al; (Zn,Cd)S:Cu,Cl+(Zn,Cd)S:Ag,Cl; $Y_2SiO_5$:Tb; $Y_2OS$:Tb; $Y_3(Al,Ga)_5O_{12}$:Ce, $Y_3(A_1,Ga)_5O_{12}$:Tb, $InBO_3$:Tb, $InBO_3$:Eu, $InBO_3$:Tb+$InBO_3$:Eu, $InBO_3$:Tb+$InBO_3$:Eu+ZnS:Ag, $(Ba,Eu)Mg_2Al_{16}O_{27}$, $(Ce,Tb)MgAl_{11}O_{19}$, $BaMgAl_{10}O_{17}$:Eu,Mn, $BaMg_2Al_{16}O_{27}$:Eu(II), $BaMgAl_{10}O_{17}$:Eu,Mn, $BaMg_2Al_{16}O_{27}$:Eu(II),Mn(II), $Ce_{0.67}Tb_{0.33}MgAl_{11}O_{19}$:Ce,Tb, $Zn_2SiO_4$:Mn,$Sb_2O_3$, $CaSiO_3$:Pb,Mn, $CaWO_4$ (Scheelite), $CaWO_4$:Pb, $MgWO_4$, $(Sr,Eu,Ba,Ca)_5(PO_4)_3$Cl, $Sr_5Cl(PO_4)_3$:Eu(II), $(Ca,Sr,Ba)_3(PO_4)_2Cl_2$:Eu, $(Sr,Ca,Ba)_{10}(PO_4)_6Cl_2$:Eu, $Sr_2P_2O_7$: Sn(II), $Sr_6P_5BO_{20}$:Eu, $Ca_5F(PO_4)_3$: Sb, $(Ba,Ti)_2P_2O_7$:Ti, $3Sr_3(PO_4)_2.SrF_2$:Sb,Mn; $Sr_5F(PO_4)_3$: Sb,Mn; $Sr_5F(PO_4)_3$:Sb,Mn; $LaPO_4$: Ce,Tb; $(La,Ce,Tb)PO_4$, $(La,Ce,Tb)PO_4$:Ce,Tb; $Ca_3(PO_4)_2.CaF_2$: Ce,Mn; $(Ca,Zn,Mg)_3(PO_4)_2$: Sn; $(Zn,Sr)_3(PO_4)_2$:Mn; $(Sr,Mg)_3(PO_4)_2$: Sn; $(Sr,Mg)_3(PO_4)_2$:Sn(II); $Ca_5F(PO_4)_3$: Sb,Mn; $Ca_5(F,Cl)(PO_4)_3$:Sb,Mn; $(Y,Eu)_2O_3$, $Y_2O_3$:Eu(III); $Mg_4(F)GeO_6$:Mn; $Mg_4(F)(Ge,Sn)O_6$:Mn; $Y(P,V)O_4$:Eu; $YVO_4$:Eu; $Y_2O_2S$:Eu; $3.5MgO_{0.5}MgF_2$ $GeO_2Mn$; $Mg_5As_2O_{11}$:Mn; $SrAl_2O_7$:Pb; $LaMgAl_{11}O_{19}$:Ce; $LaPO_4$:Ce; $SrAl_{12}O_{19}$:Ce; $BaSi_2O_5$:Pb; $SrFB_2O_3$:Eu(II); $SrB_4O_7$:Eu; $Sr_2MgSi_2O_7$:Pb and $MgGa_2O_4$:Mn(II).

* * * * *